United States Patent
Kuo et al.

(10) Patent No.: US 6,479,499 B1
(45) Date of Patent: Nov. 12, 2002

(54) 2-PHENYL-4-QUINAZOLINONE COMPOUNDS, 2-PHENYL-4-ALKOXY-QUINAZOLINE COMPOUNDS AND THEIR PHARMACEUTICAL COMPOSITIONS

(75) Inventors: Sheng-Chu Kuo, Taichung (TW); Mann-Jen Hour, Taichung (TW); Li-Jiau Huang, Taichung (TW); Kuo-Hsiung Lee, Chapel Hill, NC (US)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/605,618

(22) Filed: Jun. 28, 2000

(51) Int. Cl.7 .................. C07D 239/91; A61K 31/517
(52) U.S. Cl. ................ 514/259; 514/232.5; 514/234.5; 544/80; 544/116; 544/29
(58) Field of Search .................. 544/289, 80, 116; 514/259, 232.5, 234.5

(56) References Cited

U.S. PATENT DOCUMENTS 4,159,330 A * 6/1979 Poria ........................ 424/251
6,103,729 A * 8/2000 Rhee et al. ................ 514/262

\* cited by examiner

Primary Examiner—John M. Ford
(74) Attorney, Agent, or Firm—Jackson Walker L.L.P.

(57) ABSTRACT

Two series of 6,7,2',3',4',5'-substituted 2-phenyl-4-quinazolinones and 6,2',3',4',5'-substituted 2,3-dihydro-2-phenyl-4-quinazolinones are synthesized and evaluated for cytotoxicity against a panel of human tumor cell lines, such as epidermoid carcinoma of the nasopharynx (KB), lung carcinoma (A-549), ileocecal carcinoma (HCT-8), breast cancer (MCF-7), melanoma (SKMEL-2), ovarian cancer (1A9), glioblastoma (U-87-MG), bone (HOS), P-gp-expressing epidermoid carcinoma of the nasopharynx (KB-VIN), and prostate cancer (PC3) cell lines, and some of the compounds are found potent. The present invention also synthesizes 2-phenyl-4-alkoxy-quinazoline compounds, wherein some of the compounds exhibit antiplatelet activity.

27 Claims, No Drawings

2-PHENYL-4-QUINAZOLINONE COMPOUNDS, 2-PHENYL-4-ALKOXY-QUINAZOLINE COMPOUNDS AND THEIR PHARMACEUTICAL COMPOSITIONS

FIELD OF THE INVENTION

The present invention relates to a series of substituted 2-phenyl-4-quinazolinones compounds and substituted 2-phenyl4-alkoxy-quinazoline compounds; and in particular to their uses in treating human cancers and in inhibiting platelet aggregation.

BACKGROUND OF THE INVENTION

Microtubules provide an important framework defining cellular morphology and are essential in the division and transport of cellular chromosomes. Consequently, the microtubule has become an important target for the design of new antimitotic anticancer agents. The antimitotic agents currently in clinical use include vinca alkaloids [Rowinsky, E. K.; Donehower, R. C. The clinical pharmacology and use of antimicrotubule agents in cancer chemotherapeutics. *Pharmacol. Ther.* 1992, 52, 35–84], which inhibit microtubule polymerization, and taxoids, which promote microtubule assembly [Verweij, J.; Clavel, M.; Chevalier, B. Paclitaxel (Taxol) and docetaxel (Taxotere): not simply two of a kind. *Ann. Oncol.* 1994, 5, 495–505]. Colchicine is another well-known antimitotic agent; however, being too toxic to be used as anticancer agent, it is used clinically only as an antigout agent [Hastie, S. B. Interactions of colchicine with tubulin. *Pharmacol. Ther.* 1991, 51, 377–401; Brossi,A; Yeh, H. J.; Chrzanowska, M.; Wolff, J.; Hamel, E.; Lin, C. M.; Quinn, F.; Suffness, M.; Silverton, J. Colchicine and its analogues: recent findings. Med. Res. Rev 1988, 8, 77–94].

In recent years, some of the inventors of the present application and their co-workers have designed and synthesized three type of heterocyclic ketones, the 2-phenyl4-qinolones (PQ), 2,3-dihydro-2-phenyl-4-quinolones (DHPQ) and 2-phenyl-1,8-naphthyridin4-ones (PN) as novel antimitotic agents and have established a preliminary structure-activity relationships [Brossi, A.; Yeh, H. J.; Chrzanowska, M.; Wolff, J.; Hamel, E.; Lin, C. M.; Quinn, F.; Suffness, M.; Silverton, J. Colchicine and its analogues: recent findings. *Med. Res. Rev.* 1988, 8, 77–94; Kuo, S. C.; Lee, H. Z.; Juang, J. P.; Lin, Y. T.; Wu, T. S.; Chang, J. J.; Ledniced, D.; Paull, K. D.; Lin, C. M.; Hamel, E.; Lee, K. H. Synthesis and cytotoxicity of 1,6,7,8 and 4'-substituted 2-phenyl-4-quinolones and related compounds: identification as antimitotic agents interacting with tubulin. *J. Med. Chem.* 1993, 36, 1146–1156; Li, L.; Eang, H. K.; Kuo, S. C.; Lednicer, D.; Lin, C. M.; Hamel, E.; Lee, K. H. 2',3',4',5', 5,6,7-Substituted 2-phenyl-4-quinolones and related compounds: their synthesis, cytotoxicity, and inhibition of tubulin polymerization. *J. Med. Chem.* 1994, 37 (8),1126–1135; Li, L.; Wang, H. K.; Kuo, S. C.; Wu, T. S.; Mauger, A.; Lin, C. M.; Hamel, E.; Lee, K. H. Synthesis and biological evaluation of 3',6',7-substituted 2-phenyl4-quinolones as antimitotic antitumor agents. *J. Med. Chem.* 1994, 37 (20), 3400–3407;Xia, Y.; Yang, Z. Y.; Xia, P.; Bastow, K. F.; Tachibana, Y.; Kuo, S. C.; Hamel, E.; Hackl, T.; Lee, K. H. Synthesis and biological evaluation of 6,7,2',3',4'-substituted-1,2,3,4-tetrahydro-2-phenyl-4-quinolones as a new class of antimitotic agents. *J. Med. Chem.* 1998, 41 (7), 1155–1162; Xia, Y; Yang, Z. Y.; Xia, P.; Bastow, K. F.; Tachibana, Y.; Kuo, S. C.; Hamel, E.; Hackl, T.; Lee, K. H. Synthesis and biological evaluation of 6,7,2',3',4'-substituted-1,2,3,4-tetrahydro-2-phenyl-4-quinolones as a new class of antimitotic agents. *J. Med. Chem.* 1998, 41 (7), 1155–1162; Chen, K.; Kuo, S. C.; Hsih, M. C.; Mauger, A.; Lin, C. M.; Hamel, E.; Lee, K. H. 2',3',4',5,6,7-Substituted 2-phenyl-1,8-naphthyridin-4-ones: their synthesis, cytotoxicity, and inhibition of tubulin polymerization. *J. Med. Chem.* 1996, 40 (14), 2266–2275; Chen, K.; Kuo, S. C.; Hsih, M. C.; Mauger, A.; Lin, C. M.; Hamel, E.; Lee, K. H. Synthesis and biological evaluation of substituted 2-aryl-1,8-naphthyridin-4(1H)-ones as antimitotic antitumor agents that inhibit tubulin polymerization. *J. Med. Chem.* 1997, 40 (19), 3049–3056.]. The structures of PQ, DHPQ and PN are shown as follows:

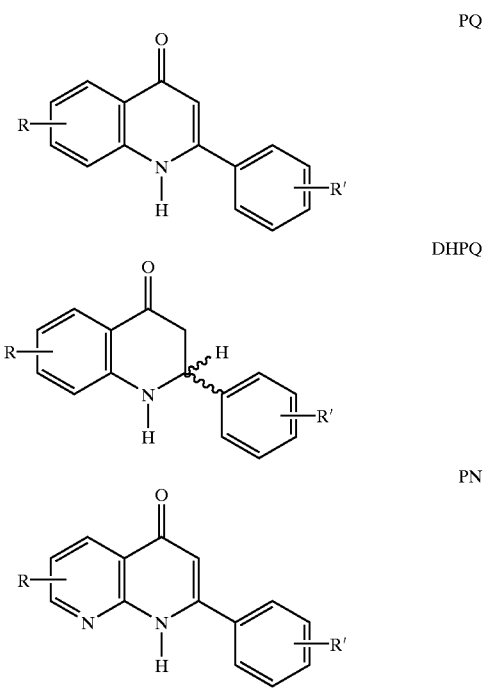

Among these three types of heterocyclic ketones, the common structural feature is a biaryl system composed of A- and C-rings that are linked by an interposed B-ring or sometimes by a hydrocarbon bridge. However, some minor structural differences also exist.

In the PQ system, when functional groups with nonbonding electrons, e.g. —$OCH_3$, —O—$CH_2$—O—, —NRR', Cl and F ($PQ_{1-6}$), were placed at the 6-position of the A-ring and the 3'-position of the C-ring, activity was very potent. These two functional groups are about 10 to 11 Å apart, and these two groups possibly may interact with the tubulin binding domain by acting as H-receptors. Thus, they might contribute significantly to the potency of PQ compounds. In the DHPQ system, the 6- and 3'-substituents ($DHPQ_1$) also plays a decisive role in activity. However, in the PN system, when the 3'-substituent is fixed (e.g. $OCH_3$), the identity of the 6-substituent e.g. H (PN-1), $CH_3$ (PN-2) or Cl (PN-3), does not noticeably affect activity. This finding is unique to the PN system and differentiates it from the PQ and DHPQ systems. The structures of PQI to PQ6, PN-1 to PN-3 and $DHPQ_1$ are shown in the followings:

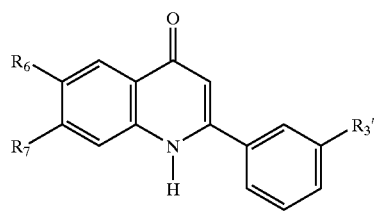

PQ

R₆ = OCH₃, R₃' = OCH₃    PQ1
R₆, R₇ = OCH₃, R₃' = OCH₃    PQ2
R₆ = F, R₃' = OCH₃    PQ3
R₆ = Cl, R₃' = OCH₃    PQ4
R₆, R₇ = OCH₂O, R₃' = NRR'    PQ5
R₆, R₇ = OCH₂O, R₃' = F    PQ6

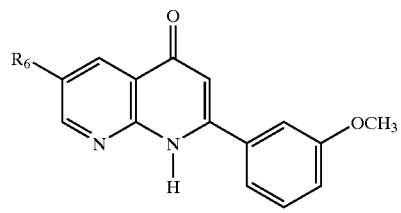

PN

R₆ = H    PN1
R₆ = CH₃    PN2
R₆ = Cl    PN3

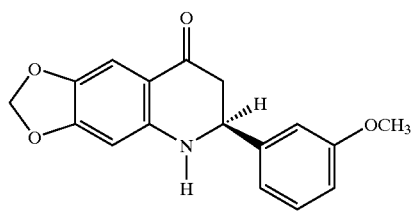

DHPQ1

The antitumor activities of 2,3-dihydro-2-aryl-4-quinazolinones (DHPQZ) were reported around 1970 [Yale, H. J.; Kalkstein, M. Substituted 2,3-dihydro-4(1H)-quinazolinones. A new class of inhibitors of cell multiplication. *J. Med. Chem.* 1967, 10, 334–336; Neil, G. L.; Li, L. H.; Buskirk, H. H.; Moxicy, T. E. Antitumor effects of the antisperrnatogenic agent, 2,3-dihydro-2-(1-naphthyl)-4 (1H)-quinazolinones. *Cancer Chemother.* 1972,56, 163–173]. Amore recent reevaluation of this type of compounds by NCI against human tumor cell lines reconfirmed that, like colchicine, they are effective inhibitors of tubulin polymerization [Hamel, E.; Lin, C. M.; Plowman, J.; Wang, H. K.; Lee, K. H.; Paull, K. D. Antitumor 2,3-dihydro-2-(aryl)-4(1H)-quinazolinone derivatives. Interactions with tubulin. *Biochem. Pharmacol.* 1996, 51, 53–59]. At the same time, 2-styrylquinazolin-4-ones (SQZ) were also identified as potent inhibitors of tubulin polymerization [Jiang, J. B.; Hesson, D. P.; Dusak, B. A.; Dexter, D. L.; Kang, G. J.; Hamel, E. Synthesis and biological evaluation of 2-styryl-quinazolin-4(3H)-ones, a new class of antimitotic anticancer agents which inhibit tubulin polymerization. *J. Med. Chem.* 1990, 33, 1721–1728; Lin, C. M.; Kang, G. J.; Roach, M. C.; Jiang, J. B.; Hesson, D. P.; Luduena, R. F.; Hamel, E. Investigation of the mechanism of the interaction of tubulin with derivatives of 2-styrylquinazolin-4(3H)-one. *Mol. Pharmacol.* 1991, 40, 827–832.]. DHPQZ and SQZ compounds have the following structures:

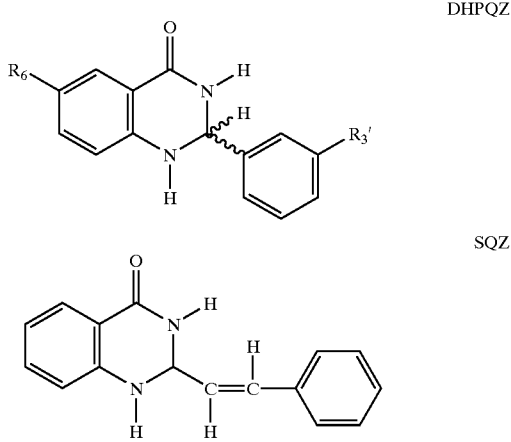

DHPQZ

SQZ

SUMMARY OF THE INVENTION

The present invention synthesizes compounds having the structures of the following formulas (I) to (IV):

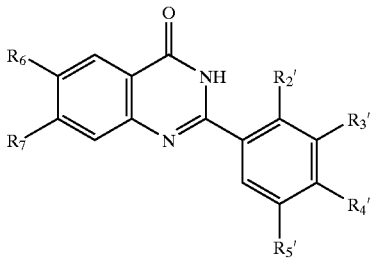

(I)

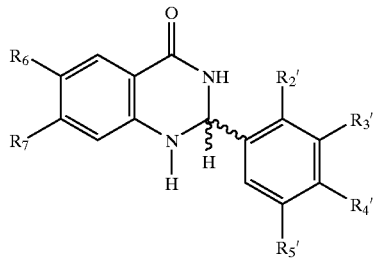

(II)

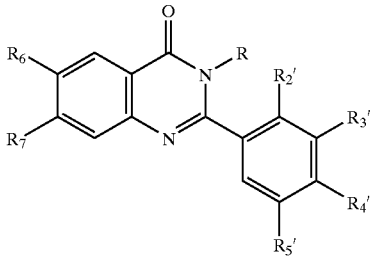

(III)

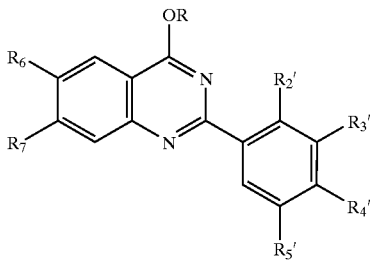

(IV)

wherein
$R_{2'}$, $R_{3'}$, $R_{4'}$, and $R_{5'}$ independently are H, $(CH_2)_nCH_3$, OH, $O(CH_2)_nCH_3$, X, or $NR_8R_9$, wherein n is an integer of 0–4, X is F, Cl, or Br, and $R_8$ and $R_9$ independently are H or $(CH_2)_nCH_3$, wherein n is defined as above;

R is $(CH_2)_nCH_3$ or $(CH_2)_nCOO(CH_2)_nCH_3$, wherein n is defined as above; and $R_6$ and $R_7$ independently are H, $(CH_2)_nCH_3$, OH, $O(CH_2)_nCH_3$, X, $NR_8R_9$,

or $R_6$ and $R_7$ together is —$OCH_2O$—, wherein n, X, $R_8$ and $R_9$ are defined as above.

The compounds (I) and (II) were evaluated for cytotoxicity and as inhibitors of tubulin polymerization in the present invention. Some of them show potent cytotoxicity against a panel of human tumor cell lines and show potent inhibition of tubulin polymerization, and thus have great potential to be used as a therapeutically effective component in a pharmaceutical composition for treating cancer.

The compounds (III) and (IV) were found potent in inhibiting aggregation of platelet in the present invention, and thus are useful as a therapeutically effective component in a pharmaceutical composition for inhibiting aggregation of platelet.

DETAILED DESCRIPTION OF THE INVENTION

In one aspect of the present invention a series of 6,7,2',3',4',5'-substituted 2-phenyl-4-quinazolones having the formula (I) are synthesized:

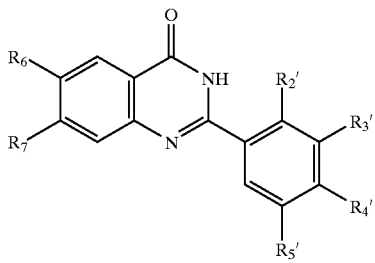

(I)

wherein $R_{2'}$, $R_{3'}$, $R_{4'}$, $R_{5'}$, $R_6$ and $R_7$ are defined as above.

Preferably, $R_{2'}$, $R_{3'}$, $R_{4'}$ and $R_{5'}$ in the formula (I) independently are H or $O(CH_2)_nCH_3$, and at least one of $R_{2'}$, $R_{3'}$, $R_{4'}$ and $R_{5'}$ is $O(CH_2)_nCH_3$, wherein n is defined as above. More preferably, $R_{2'}$, $R_{4'}$ and $R_{5'}$ are H, and $R_{3'}$ is methoxy.

Preferably, $R_6$ and $R_7$ in the formula (I) independently are H, $O(CH_2)_nCH_3$, X, $NR_8R_9$,

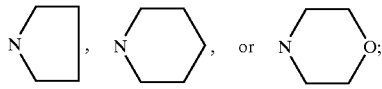

or $R_6$ and $R_7$ together is —$OCH_2O$—, wherein n, X, $R_8$ and $R_9$ are defined as in claim 1. More preferably, $R_6$ and $R_7$ independently are H, $O(CH_2)_nCH_3$, X, $NR_8R_9$,

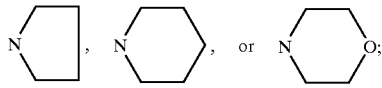

or R6 and $R_7$ together is —$OCH_2O$—, wherein n, X, $R_8$ and $R_9$ are defined as above. Most preferably, $R_7$ is H, and $R_6$ is $NR_8R_9$,

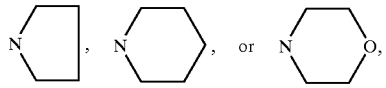

wherein $R_8$ and $R_9$ are defined as above, and preferably, $R_8$ and $R_9$ are methyl Preferably, $R_6$ and $R_7$ in the formula (I) independently are H, methoxy or X, wherein X is defined as above.

In another aspect, the present invention provides a series of 6,7,2',3',4',5'-substituted 2,3-dihydro-2-phenyl4-quinazolones having the following formula (II):

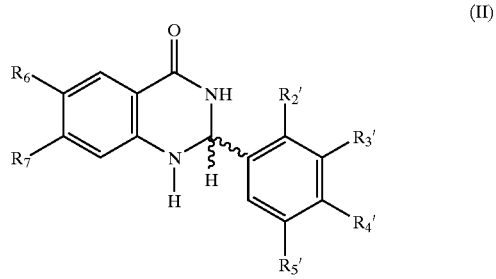

(II)

wherein $R_{2'}$, $R_{3'}$, $R_{4'}$, $R_{5'}$, $R_6$ and $R_7$ are defined as above.

Preferably, $R_7$ in the formula (II) is H.

Preferably, $R_{2'}$, $R_{3'}$, $R_{4'}$ and $R_{5'}$ in the formula (II) independently are H or $O(CH_2)_nCH_3$, provided that at least one of them is $O(CH_2)_nCH_3$, wherein n is defined as above. More preferably, $R_{2'}$, $R_{4'}$ and $R_{5'}$ are H, and $R_{3'}$ is methoxy.

Preferably, $R_6$ in the formula (II) is X, wherein X is defined as above. More preferably, wherein X is Cl.

In further another aspect, the present invention provides a series of 3,6,7,2',3',4',5'-substituted 2-phenyl-4-quinazolones having the following formula (III) and a series of 6,7,2',3',4',5'-substituted 2-phenyl-4-alkoxy-quinazolines (IV):

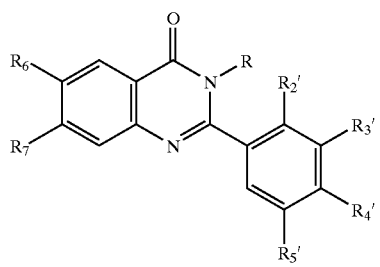

(III)

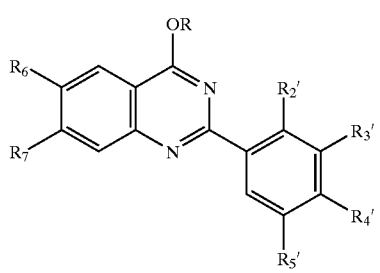

(IV)

wherein $R_{2'}$, $R_{3'}$, $R_{4'}$, $R_{5'}$, R, $R_6$ and $R_7$ are defined as above.

Preferably, $R_{5'}$, $R_6$ and $R_7$ in the formulas (III) and (IV) are all H.

Preferably, n in the formulas (III) and (IV) is 0 or 1.

Preferably, R in the formulas (III) and (IV) is $(CH_2)_nCH_3$, wherein n is 0 or 1, and preferably n is 1.

Preferably, $R_{2'}$, $R_{3'}$, and $R_{4'}$ in the formulas (III) and (IV) independently are H or $OCH_3$. More preferably, $R_{2'}$, $R_{3'}$, and $R_{4'}$ are all H. Alternatively, $R_{2'}$ and $R_{3'}$ are both H, and $R_{4'}$ is $OCH_3$.

The present invention also discloses a pharmaceutical composition for the treatment of cancer, which comprises a therapeutically effective amount of a compound of the formula (I) or (II) or a pharmaceutically acceptable salt thereof, as an active ingredient, in admixture with a pharmaceutically acceptable carrier or diluent for the active ingredient.

The present invention also provides a method of treating a cancer comprising administering a therapeutically effective amount of a compound of the formula (I) or (II) to a subject suffering from cancer.

The present invention also discloses a pharmaceutical composition for the inhibition of aggregation of platelet, which comprises a therapeutically effective amount of a compound of the formula (III) or (IV), preferably the formula (III), or a pharmaceutically acceptable salt thereof, as an active ingredient, in admixture with a pharmaceutically acceptable carrier or diluent for the active ingredient.

The present invention also provides a method of inhibiting an aggregation of platelet in a patient comprising administering a therapeutically effective amount of a compound of the formula (III) or (IV), preferably the formula (III), to said patient.

DETAILED DESCRIPTION OF THE INVENTION

The starting 4,5-substituted 2-aminobenzamides (3, 10–11, 16, 25–29), needed for the synthesis of our target compounds, were prepared according to Schemes 1–4. As shown in Scheme 1, 2-amino-5-fluoro-benzamide (3) was prepared by treating commercially available 2-amino-5-fluoro-benzoic acid (1) first with $SOCl_2$, then with ammonia. In Scheme 2, the 4-methoxy and 4,5-dimethoxy-2-aminobenzaimdes (10, 11) were prepared by converting the —COOH group of the starting 2-nitrobenzoic acids (4, 5) to —$CONH_2$ (8, 9) followed by reduction of the 2-$NO_2$ group to 2-$NH_2$ (10, 11). In the same manner, 4,5-methylenedioxy-2-aminobenzamide (16) was obtained from 4,5-methylenedioxy-2-nitrobenzoic acid (13) after oxidation of the —CHO group of 4,5-methylenedioxy-2-nitrobenzaldehyde (12) (Scheme 3). Finally, according to Scheme 4, 6-alkylamino-2-aminobenzamides (25–29) were prepared by first converting the —COOH group of 5-chloro-2-nitrobenzoic acid (17) to —$CONH_2$ (19) followed by nucleophilic displacement of the 5-chloro group by different secondary amines, and subsequent hydrogenation.

As illustrated in Scheme 5, target compounds 41–59 were prepared by reacting the above starting materials (3, 10–11, 16, 25–29, respectively) with methoxybenzaldehydes (33–40) in N,N-dimethylacetamide (DMAC) in the presence of $NaHSO_3$. Thermal cyclodehydration/dehydrogenation resulted in substituted 2-phenyl-4-quinazolinones (41–59) in high yields.

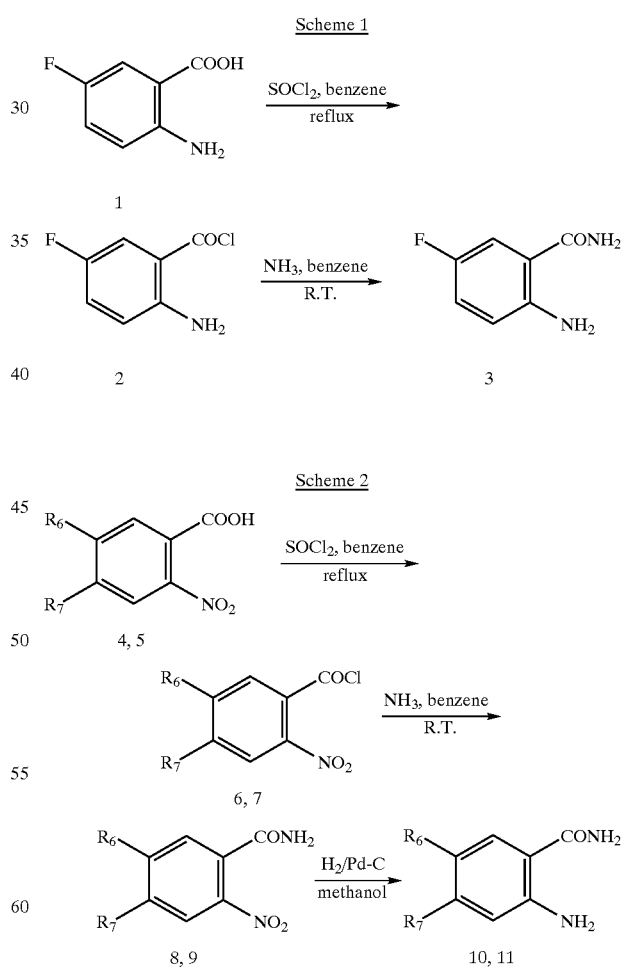

Scheme 3

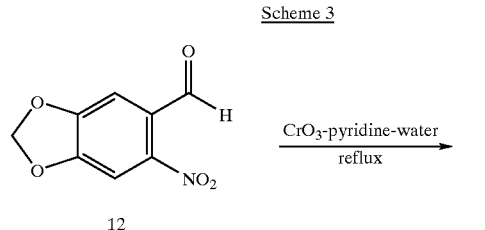

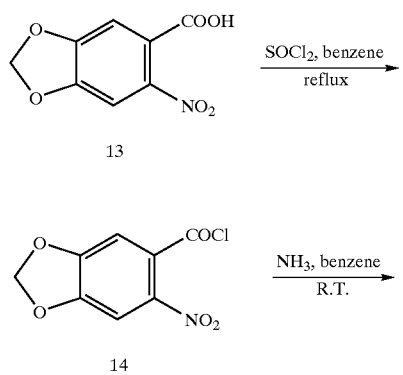

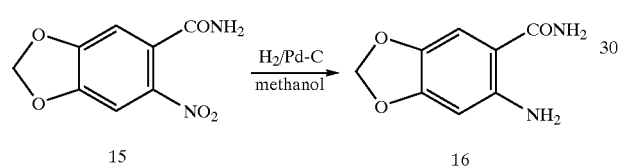

Scheme 4

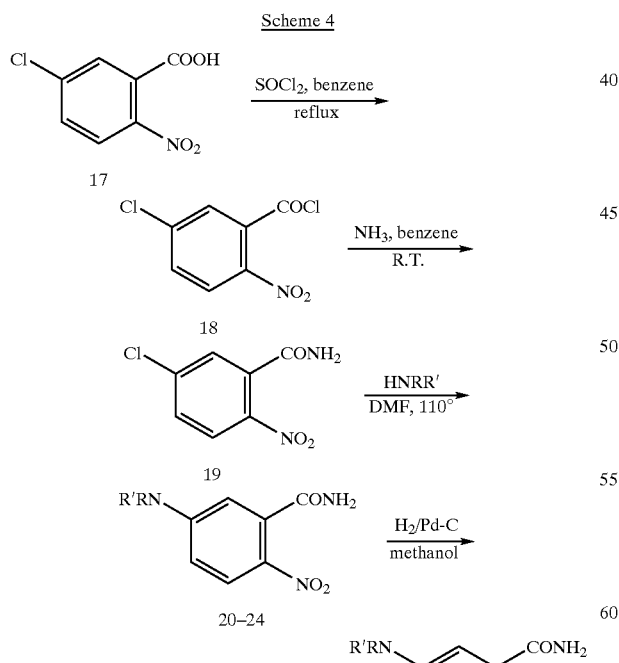

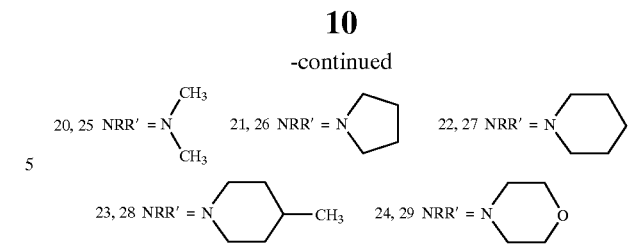

20, 25 NRR' = N(CH₃)₂    21, 26 NRR' = pyrrolidinyl    22, 27 NRR' = piperidinyl 23, 28 NRR' = 4-methylpiperidinyl    24, 29 NRR' = morpholinyl Scheme 5

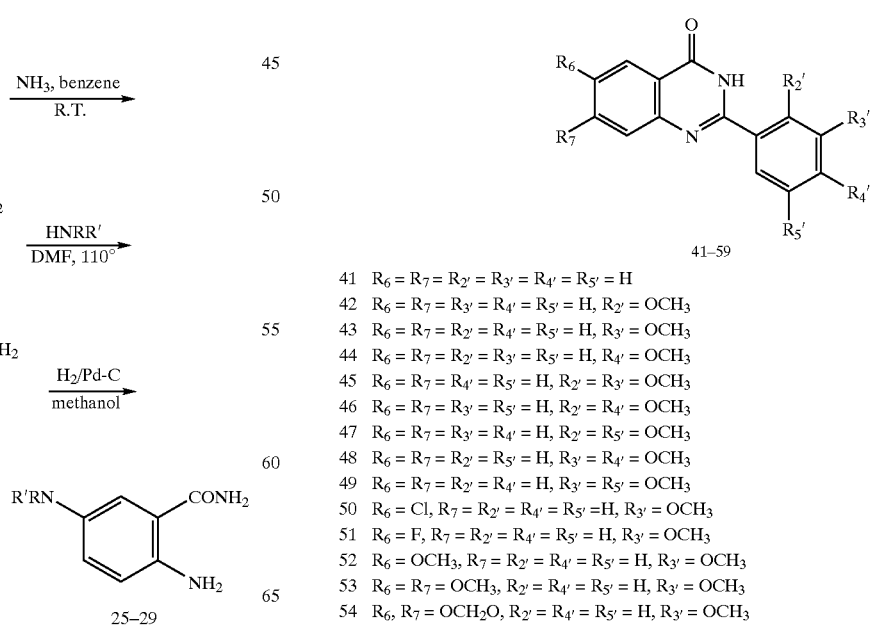

30   $R_6 = R_7 = H$
31   $R_6 = Cl, R_7 = H$

32   $R_{2'} = R_{3'} = R_{4'} = R_{5'} = H$
33   $R_{3'} = R_{4'} = R_{5'} = H, R_{2'} = OCH_3$
34   $R_{2'} = R_{3'} = R_{5'} = H, R_{3'} = OCH_3$
35   $R_{3'} = R_{4'} = R_{5'} = H, R_{4'} = OCH_3$
36   $R_{3'} = R_{5'} = H, R_{2'} = R_{3'} = OCH_3$
37   $R_{3'} = R_{5'} = H, R_{2'} = R_{4'} = OCH_3$
38   $R_{3'} = R_{4'} = H, R_{2'} = R_{5'} = OCH_3$
39   $R_{2'} = R_{5'} = H, R_{3'} = R_{4'} = OCH_3$
40   $R_{2'} = R_{4'} = H, R_{3'} = R_{5'} = OCH_3$

41   $R_6 = R_7 = R_{2'} = R_{3'} = R_{4'} = R_{5'} = H$
42   $R_6 = R_7 = R_{3'} = R_{4'} = R_{5'} = H, R_{2'} = OCH_3$
43   $R_6 = R_7 = R_{2'} = R_{4'} = R_{5'} = H, R_{3'} = OCH_3$
44   $R_6 = R_7 = R_{2'} = R_{3'} = R_{5'} = H, R_{4'} = OCH_3$
45   $R_6 = R_7 = R_{4'} = R_{5'} = H, R_{2'} = R_{3'} = OCH_3$
46   $R_6 = R_7 = R_{3'} = R_{5'} = H, R_{2'} = R_{4'} = OCH_3$
47   $R_6 = R_7 = R_{3'} = R_{4'} = H, R_{2'} = R_{5'} = OCH_3$
48   $R_6 = R_7 = R_{2'} = R_{5'} = H, R_{3'} = R_{4'} = OCH_3$
49   $R_6 = R_7 = R_{2'} = R_{4'} = H, R_{3'} = R_{5'} = OCH_3$
50   $R_6 = Cl, R_7 = R_{2'} = R_{4'} = R_{5'} = H, R_{3'} = OCH_3$
51   $R_6 = F, R_7 = R_{2'} = R_{4'} = R_{5'} = H, R_{3'} = OCH_3$
52   $R_6 = OCH_3, R_7 = R_{2'} = R_{4'} = R_{5'} = H, R_{3'} = OCH_3$
53   $R_6 = R_7 = OCH_3, R_{2'} = R_{4'} = R_{5'} = H, R_{3'} = OCH_3$
54   $R_6, R_7 = OCH_2O, R_{2'} = R_{4'} = R_{5'} = H, R_{3'} = OCH_3$

-continued

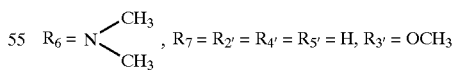

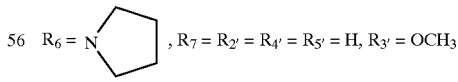

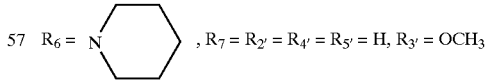

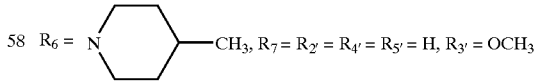

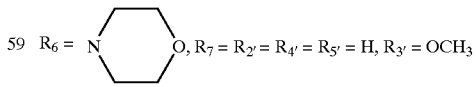

Scheme 6

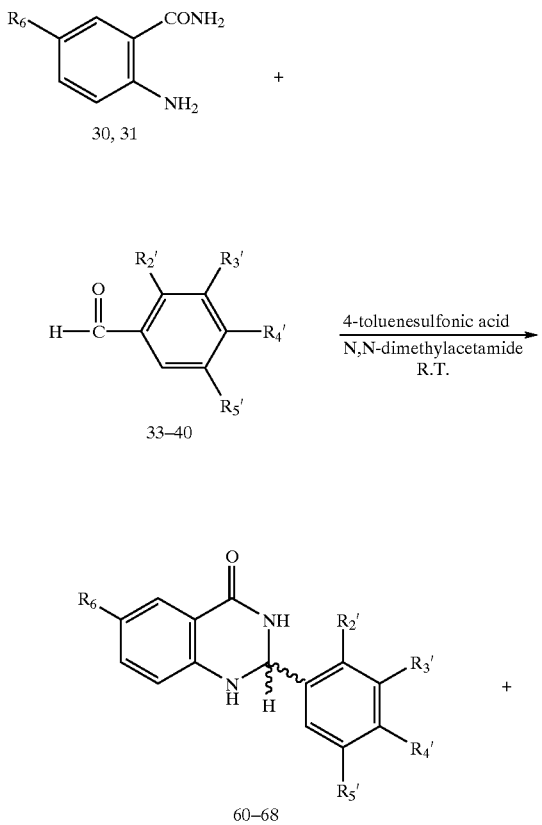

60  $R_6 = R_{3'} = R_{4'} = R_{5'} = H, R_{2'} = OCH_3$
61  $R_6 = R_{2'} = R_{4'} = R_{5'} = H, R_{3'} = OCH_3$
62  $R_6 = R_{2'} = R_{3'} = R_{5'} = H, R_{4'} = OCH_3$
63  $R_6 = R_{4'} = R_{5'} = H, R_{2'} = R_{3'} = OCH_3$
64  $R_6 = R_{3'} = R_{5'} = H, R_{2'} = R_{4'} = OCH_3$
65  $R_6 = R_{3'} = R_{4'} = H, R_{2'} = R_{5'} = OCH_3$
66  $R_6 = R_{2'} = R_{5'} = H, R_{3'} = R_{4'} = OCH_3$
67  $R_6 = R_{2'} = R_{4'} = H, R_{3'} = R_{5'} = OCH_3$
68  $R_6 = Cl, R_{2'} = R_{4'} = R_{5'} = H, R_{3'} = OCH_3$

-continued

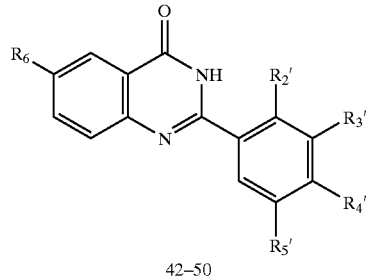

42–50

The synthesis of 2,3-dihydro-2-phenyl-4-quinazolinones (60–68) is described in Scheme 6. The preparation of 2,3-dihydro-3'-methoxy-2-phenyl-4-quinazolinone (61) is detailed below as an example.

First, a mixture of 2-aminobenzamide (30) and 3-methoxybenzaldehyde (34) in DMAc was heated to 80° C. for 1 hr. Subsequent purification with column chromatography afforded 61 (mp 148–150° C.) and 43 (mp 177–179° C.) in yields of 75% and 15%, respectively. The chemical structure of 43 was confirmed by IR, NMR and MS spectral analysis as 3'-methoxy-2-phenyl-4-quinazolinone. For 61, the molecular formula was determined by elemental and MS analysis (m/z 254, M$^+$) as $C_{15}H_{14}N_2O_2$, which matches the expected 2,3-dihydro-3'-methoxy-2-phenyl-4-quinazolinone. The $^1$H NMR of 61 showed three additional proton signals not seen in the spectrum of 43: 5.73 (H-2), 7.15 (N$_1$—H) and 8.34 (N$_3$—H). The 2D HMBC spectrum of 61 showed the expected long range coupling between H-2 and C-4 ($\delta$163.77), C-8a ($\delta$147.98), C-2' ($\delta$119.11) and C-6' ($\delta$112.75). All spectral data confirmed our assignment of 61 as 2,3-dihydro-3'-methoxy-2-phenyl-4-quinazolinone.

In order to increase the yield of 61, reaction conditions were adjusted to minimize the unwanted dehydrogenation of 61 and convertism to 43. First, we lowered the reaction temperature to 25±2° C. and extended the reaction time to 4 hr. However, these conditions only resulted in a lower conversion as indicated by the considerable amount of starting materials (30, 34) detected by TLC in the reaction mixture. Next, we again carried out the reaction, at 25±2° C. in DMAC, but also incorporated a catalytic amount of p-toluenesulfonic acid. The reaction was completed in 30 min and the subsequent work up resulted in high yield (89.0%) of 61 and minor yield (4.0%) of 43. Consequently, the same reaction condition was adopted in the subsequent preparation of 60 and 62–68, and resulted in high yields of all desired products.

Thus, all 2,3-dihydro products (60–68) have been prepared as racemic mixtures. Resolution of these racemic mixtures has not been attempted in this work, but will be pursued if unusual biological activity is found in our forthcoming studies.

We also used various benzamides (10–11, 16, 25–29) with electron donating groups (e.g. —OCH$_3$, —OCH$_2$O—, —NRR') on the benzene ring as starting materials. Unexpectedly, instead of obtaining our desired 2,3-dihydro products, the corresponding dehydrogenated products (52–59) were produced in high yields. TLC check analysis of the crude products did show materials resembling the expected 2,3-dihydro derivatives. However, they were readily converted to their corresponding dehydrogenated derivatives (52–59) via spontaneous dehydrogenation during the work up procedures, such as column chromatography or recrystallization.

Finally, we used 5-fluorobenzamides (3) as starting material in the attempted preparation of 2,3-dihydro-6-fluoro-2-phenyl-4-quinazolinone. However, although F and Cl belong to the same class of electron withdrawing group, the fluorinated 2,3-dihydro derivative was much less stable than the Cl-containing counterpart (68) and readily underwent spontaneous dehydrogenation to give 51 during the final work up.

Summarizing the above results, we concluded that 2,3-dihydro-2-phenyl-4-quinazolinones containing electron donating groups or fluorine at the 6 or 7 position easily underwent spontaneous dehydrogenation. Thus, preparing these compounds for cytotoxic evaluation would be impractical, as they are readily undergo spontaneous dehydrogenation and would not be stable in the solvent required for biological testing.

The synthetic pathway for target compounds, 69–76, and 77–81 series, were illustrated in Scheme 7, the synthesis of two representing samples (69, 77) was detailed below.

The starting material, 2-phenyl-4-quinazolinone (41) was treated with NaH in THF, followed by methylation with methyl iodide to give 69 (mp 50–51° C.) and 77 (mp 125–127° C.) in the yield ratio of 1:2.2. From the elemental analysis and mass spectral data (m/z 236), their molecular formulae were both determined as $C_{15}H_{12}N_2O$. This result led to our assumption that they might be O-methyl and N-methyl isomers, such assumption was proven to be supported by their $^1$H-NMR spectral evidence, in which the signal of methyl group for compound 69 at δ4.26 was assigned to $OCH_3$ protons. In contrast, the signal of methyl group for compound 77 at δ3.47 was attributed to its N-methyl protons. Furthermore, we compared their HMBC spectra of 2D NMR and found that the O-methyl protons of 69 exhibited long range coupling only with C-4 (δ167.00), whereas the $N^3$-methyl protons of 77 showed long range coupling with both C-2 (δ156.10) and C-4 (δ162.76). Based on the above spectral evidence, we confirmed 69 as 4-methoxy-2-phenylquinazoline and 77 as $N^3$-methyl-2-phenyl-4-quinazolinone.

Following similar synthetic procedures for 69 and 77, compound 41 was subjected to alkylation by ethyl iodide and ethyl bromoacetate respectively, to yield primarily O-ethyl (70) and O-ethoxycarbonylmethyl (71) derivatives respectively. Some minor yield of $N^3$-ethyl (78) and $N^3$-ethoxycarbonylmethyl derivatives (79), respectively, was also found.

Next, when ethyl 4-chlorobutyrate and ethyl 5-bromovalerate were used separately in the alkylation of compound 41, only their corresponding O-alkylated derivatives (72, 73) were produced, and no trace of N-alkylated products were detectable by TLC.

Again, when using 2',3',4'-substituted 2-phenyl-4-quinazolinones (42–44) as the starting materials, their ethylation products were found to be mainly, their corresponding O-ethyl derivatives (74–76), although small quantity of their corresponding N-ethyl products (80–81) were also present.

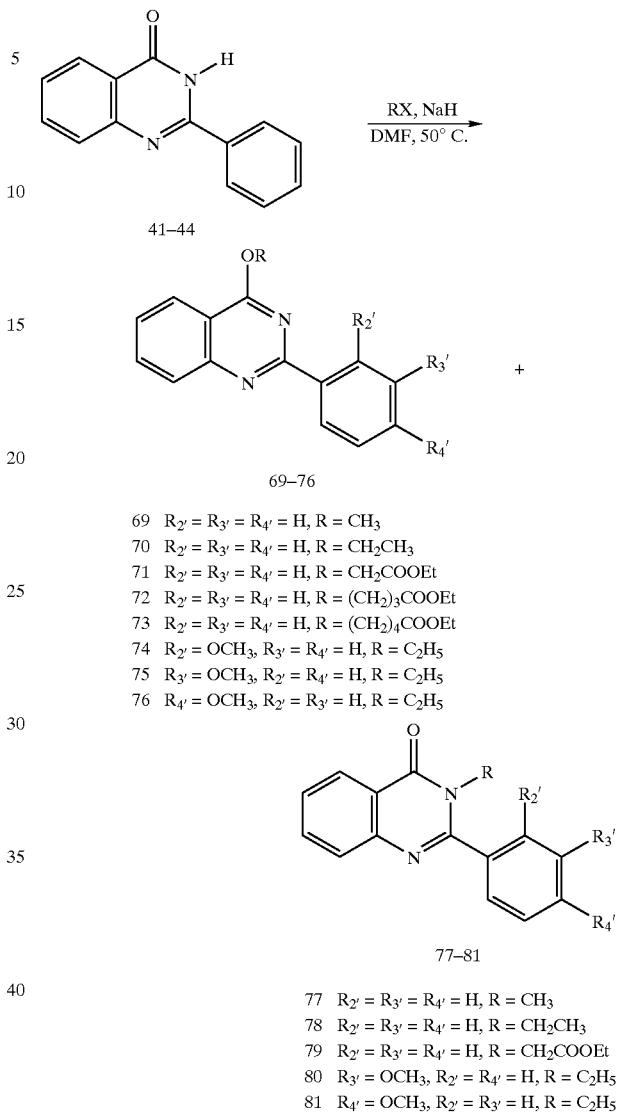

Scheme 7

41–44

69–76

69  $R_{2'} = R_{3'} = R_{4'} = H, R = CH_3$
70  $R_{2'} = R_{3'} = R_{4'} = H, R = CH_2CH_3$
71  $R_{2'} = R_{3'} = R_{4'} = H, R = CH_2COOEt$
72  $R_{2'} = R_{3'} = R_{4'} = H, R = (CH_2)_3COOEt$
73  $R_{2'} = R_{3'} = R_{4'} = H, R = (CH_2)_4COOEt$
74  $R_{2'} = OCH_3, R_{3'} = R_{4'} = H, R = C_2H_5$
75  $R_{3'} = OCH_3, R_{2'} = R_{4'} = H, R = C_2H_5$
76  $R_{4'} = OCH_3, R_{2'} = R_{3'} = H, R = C_2H_5$

77–81

77  $R_{2'} = R_{3'} = R_{4'} = H, R = CH_3$
78  $R_{2'} = R_{3'} = R_{4'} = H, R = CH_2CH_3$
79  $R_{2'} = R_{3'} = R_{4'} = H, R = CH_2COOEt$
80  $R_{3'} = OCH_3, R_{2'} = R_{4'} = H, R = C_2H_5$
81  $R_{4'} = OCH_3, R_{2'} = R_{3'} = H, R = C_2H_5$

EXPERIMENTS

A. Chemistry

Melting points were determined on a Yanaco MP-500D melting point apparatus and are uncorrected. IR spectra were recorded on Shimadzu IR-440 and Nicolet Impact 400 FT-IR spectrophotometers as KBr pellets. NMR spectra were obtained on a Bruker Avance DPX-200 FT-NMR spectrometer in DMSO-$d_6$. The following abbreviations are used: s, singlet; d, doublet; t, triplet; q, quartet; m, multiplet; and br, broad. MS spectra were measured with a VG Platform fisons instrument. The UV spectra were recorded on a Shimadzu UV-160A UV-Vis recording spectrophotometer as methanolic solutions. Elemental analyses (C, H, N) were performed at China Medical College, Taiwan and the results were within ±0.4% of the calculated values.

2-Amino-5-fluorobenzamide (3). To a suspension of 2-amino-5-fluorobenzoic acid (1) (1.0 g, 6.3 mmol) in benzene (30 ml) under reflux was added dropwise thionyl chloride (1.5 g, 12.6 mmol). The resulting mixture was stirred under reflux for 4 h, and then evaporated. The residue was dissolved in 200 ml of benzene and treated with anhydrous ammonia gas at room temperature. After removing solvent, compound 3 was obtained (0.9 g) as brown powder; MS m/z 154 (M$^+$).

2-Amino-5-methoxybenzamide (10). 5-Methoxy-2-nitrobenzoic acid (4) (1.0 g, 5.1 mmol) was treated as described for the preparation of compound 3 to give 5-methoxy-2-nitrobenzamide (8). The intermediate was then dissolved in MeOH and hydrogenated over 10% Pd/C for 6 h. The catalyst was removed by filtration, and the solution was evaporated to afford 10 (0.8 g) as brown powder; MS m/z 166 (M$^+$).

2-Amino-4,5-dimethoxybenzamide (11). According to the preparation of 10, 4,5-dimethoxy-2-nitrobenzoic acid (5) (1.0 g, 4.4 mmol) was used to afford 11 (0.8 g) as brown powder; MS m/z 196 (M$^+$).

2-Amino4,5-methylenedioxybenzamide (16). The mixture of 4,5-methylenedioxy-2-nitrobenzaldehyde (12) (1.0 g, 5.1 mmol) and Cornforth reagent (CrO$_3$-pyridine-water) (40 ml) was stirred under reflux for 4 h, and then evaporated. The solid was dissolved in water, and acidified with 10% HCl. The acidified solution was extracted with EtOAc, and dried over MgSO$_4$. After evaporation, the solid was treated as described for the preparation of 10 to afford 16 (0.7 g) as brown powder; MS m/z 180 (M$^+$).

2-Amino-5-(N,N-dimethylamino)benzamide (25). 5-Chloro-2-nitrobenzoic acid (17) (1.0 g, 4.9 mmol) was treated as described for the preparation of 3 to give 5-chloro-2-nitrobenzamide (19). The intermediate was then dissolved in DMF (10 ml), treated with dimethylamine at 110° C. for 3 h, and poured into ice water (300 ml). The precipitate was collected, washed with water, and dried in vacuo. The dried solid was then hydrogenaed as described for the preparation of 10 to afford 25 (0.6 g) as brown powder; MS m/z 179 (M$^+$).

2-Amino-5-pyrrolidinylbenzamide (26). According to the preparation of 25, pyrrolidine was used to afford 26 (0.7 g) as brown powder; MS m/z 205 (M$^+$).

2-Amino-5-piperidinylbenzamide (27). According to the preparation of 25, piperidine was used to afford 27 (0.8 g) as brown powder; MS m/z 219 (M$^+$).

2-Amino-5-(4-methylpiperidinyl)benzamide (28). According to the preparation of 25, 4-methylpiperidine was used to afford 28 (0.8 g) as brown liquid;

MS m/z 233 (M$^+$).

2-Amino-5-morpholinylbenzamide (29). According to the preparation of compound 25, morpholine was used to afford 29 (0.8 g) as brown powder; MS m/z 221 (M$^+$).

2-Phenyl-4-quinazolinone (41). Sodium hydrogen sulfite (0.8 g, 7.5 mmol) was added to a solution of 2-aminobenzamide (30) (1.0 g, 7.3 mmol) and benzaldehyde (32) (0.8 g, 7.3 mmol) in N,N-dimethylacetamide (DMAC) (20 ml). The mixture was heated with stirring at 150° C. for 2 h and then poured into ice water (200 ml). The precipitate was collected, washed with water, and then dried in vacuo. After recrystallization from EtOH, 41 was obtained (1.5 g, 92.6%) as pale yellow needles. Yield, mp, and spectral data are given in Table 1.

2-(2'-Methoxyphenyl)-4-quinazolinone (42). According to the preparation of 41, 2-methoxybenzaldehyde (33) (1.0 g, 7.3 mmol) was used to afford 42 (1.6 g, 89.1%) as pale yellow needles.

2-(3'-Methoxyphenyl)-4-quinazolinone (43). According to the preparation of 42, 3-methoxybenzaldehyde (34) (1.0 g, 7.3 mmol) was used to afford 43 (1.7 g, 95.0%) as pale yellow needles.

2-(4'-Methoxyphenyl)-4-quinazolinone (44). According to the preparation of 42, 4-methoxybenzaldehyde (35) (1.0 g, 7.3 mmol) was used to afford 44 (1.8 g, 96.4%) as pale yellow needles.

2-(2',3'-Dimethoxyphenyl)-4-quinazolinone (45). According to the preparation of 42, 2,3-dimethoxybenzaldehyde (36) (1.2 g, 7.3 mmol) was used to afford 45 (1.8 g, 86.0%) as pale yellow needles.

2-(2',4'-Dimethoxyphenyl)-4-quinazolinone (46). According to the preparation of 42, 2,4-dimethoxybenzaldehyde (37) (1.2 g, 7.3 mmol) was used to afford 46 (1.7 g, 84.3%) as pale yellow needles.

2-(2',5'-Dimethoxyphenyl)-4-quinazolinone (47). According to the preparation of 42, 2,5-dimethoxybenzaldehyde (38) (1.2 g, 7.3 mmol) was used to afford 47 (1.8 g, 88.6%) as pale yellow prism crystals.

2-(3',4'-Dimethoxyphenyl)-4-quinazolinone (48). According to the preparation of 42, 3,4-dimethoxybenzaldehyde (39) (1.2 g, 7.3 mmol) was used to afford 48 (1.8 g, 89.0%) as pale yellow prism crystals.

2-(3',5'-Dimethoxyphenyl)-4-quinazolinone (49). According to the preparation of 42, 3,5-dimethoxybenzaldehyde (40) (1.2 g, 7.3 mmol) was used to afford 49 (1.7 g, 84.0%) as pale yellow needles.

2-(3'-Methoxyphenyl)-6-chloro-4-quinazolinone (50). According to the preparation of 42, 2-amino-5-chlorobenzamide (31) (1.0 g, 5.9 mmol)and 3-methoxybenzaldehyde (34) (0.8 g, 5.9 mmol) were used to afford 50 (1.6 g, 94.3%) as pale yellow needles.

2-(3'-Methoxyphenyl)-6-fluoro-4-quinazolinone (51). According to the preparation of compound 42, 3 (1.0 g, 6.5 mmol) and 3-methoxybenzaldehyde (34) (0.9 g, 6.5 mmol) were used to afford 51 (0.8 g, 46.8%) as pale yellow needles.

2-(3'-Methoxyphenyl)-6-methoxy-4-quinazolinone (52). According to the preparation of 42, 10 (1.0 g, 6.0 mmol) and 3-methoxybenzaldehyde (34) (0.8 g, 6.0 mmol) were used to afford 52 (0.7 g, 42.4%) as pale yellow needles.

2-(3'-Methoxyphenyl)-6,7-dimethoxy-4-quinazolinone (53). According to the preparation of 42, 11 (1.0 g, 5.1 mmol) and 3-methoxybenzaldehyde (34) (0.7 g, 5.1 mmol) were used to afford 53 (0.5 g, 30.8%) as pale yellow prism crystals.

2-(3'-Methoxyphenyl)-6,7-(methylenedioxy)-4-quinazolinone (54). According to the preparation of 42, 16 (1.0 g, 5.5 mmol) and 3-methoxybenzaldehyde (34) (0.7 g, 5.5 mmol) were used to afford 54 (0.1 g, 8.8%) as pale yellow needles.

2-(3'-Methoxyphenyl)-6-(N,N-dimethylamino)-4-quinazolinone (55). According to the preparation of 42, 25 (1.0 g, 5.6 mmol) and 3-methoxybenzaldehyde (34) (0.8 g, 5.6 mmol) were used to afford 55 (0.8 g, 51.2%) as pale yellow needles.

2-(3'-Methoxyphenyl)-6-(pyrrolidinyl)-4-quinazolinone (56). According to the preparation of 42, 26 (1.0 g, 4.9 mmol) and 3-methoxybenzaldehyde (34) (0.7 g, 4.9 mmol) were used to afford 56 (0.6 g, 40.0%) as pale yellow prism crystals.

2-(3'-Methoxyphenyl)-6-(piperidinyl)-4-quinazolinone (57). According to the preparation of 42, 27 (1.0 g, 4.6 mmol) and 3-methoxybenzaldehyde (34) (0.6 g, 4.6 mmol) were used to afford 57 (0.8 g, 55.0%) as pale yellow prism crystals.

2-(3'-Methoxyphenyl)-6-(4-methylpiperidinyl)-4-quinazolinone (58). According to the preparation of 42, 28

(1.0 g, 4.3 mmol) and 3-methoxybenzaldehyde (34) (0.6 g, 4.3 mmol) were used to afford 58 (0.9 g, 57.6%) as pale yellow prism crystals.

2-(3'-Methoxyphenyl)-6-(morpholinyl)-4-quinazolinone (59). According to the preparation of 42, 29 (1.0 g, 4.5 mmol) and 3-methoxybenzaldehyde (34) (0.6 g, 4.5 mmol) were used to afford 59 (0.7 g, 48.3%) as pale yellow needles.

2,3-Dihydro-2-(3'-methoxyphenyl)-4-quinazolinone (61). Method A: 2-Aminobenzamide (30) (1.0 g, 7.3 mmol) and 3-methoxybenzaldehyde (34) (1.0 g, 7.3 mmol) were heated with stirring in DMAC (20 ml) at 80° C. for 2 h and then poured into ice water (200 ml). The precipitate was collected, washed with water, then dried and purified by column chromatography (silica gel-ethyl acetate/n-hexane) to afford 43 (0.3 g, 15.0%) and 61 (1.4 g, 75.2%) as pale yellow powder. Yield, mp, and spectral data are given in Table 1.
Method B: p-Toluenesulfonic acid monohydrate (0.1 g, 0.3 mmol) was added to a solution of 2-aminobenzamide (30) (1.0 g, 7.3 mmol) and 3-methoxybenzaldehyde (34) (1.0 g, 7.3 mmol) in DMAC (20 ml). The mixture was stirred at room temperature for 2 h and then poured into ice water (200 ml). The precipitate was collected, washed with water, then dried and purified by column chromatography (silica gel-ethyl acetate/n-hexane) to afford 43 (70.0 mg, 4.0%) and 61 (1.7 g, 89.0%) as pale yellow powder.

2,3-Dihydro-2-(2'-methoxyphenyl)-4-quinazolinone (60). According to the preparation of 61 (Method B), 2-methoxybenzaldehyde (33) (1.0 g, 7.3 mmol) was used to afford 42 (90.0 mg, 5.0%) and 60 (1.7 g, 90.1%) as pale yellow powder.

2,3-Dihydro-2-(4'-methoxyphenyl)-4-quinazolinone (62). According to the preparation of 61 (Method B), 4-methoxybenzaldehyde (35) (1.0 g, 7.3 mmol) was used to afford 44 (40.0 mg, 2.0%) and 62 (1.7 g, 93.3%) as pale yellow powder.

2,3-Dihydro-2-(2',3'-dimethoxyphenyl)-4-quinazolinone (63). According to the preparation of 61 (Method B), 2,3-dimethoxybenzaldehyde (36) (1.2 g, 7.3 mmol) was used to afford 45 (80.1 mg, 4.0%) and 63 (1.6 g, 78.1%) as pale yellow powder.

2,3-Dihydro-2-(2',4'-dimethoxyphenyl)-4-quinazolinone (64). According to the preparation of 61 (Method B), 2,4-dimethoxybenzaldehyde (37) (1.2 g, 7.3 mmol) was used to afford 46 (99.9 mg, 5.0%) and 64 (1.8 g, 86.5%) as pale yellow powder.

2,3-Dihydro-2-(2',5'-dimethoxyphenyl)-4-quinazolinone (65). According to the preparation of 61 (Method B), 2,5-dimethoxybenzaldehyde (38) (1.2 g, 7.3 mmol) was used to afford 47 (80.1 mg, 4.0%) and 65 (1.7 g, 80.3%) as pale yellow powder.

2,3-Dihydro-2-(3',4'-dimethoxyphenyl)-4-quinazolinone (66). According to the preparation of 61 (Method B), 3,4-dimethoxybenzaldehyde (39) (1.2 g, 7.3 mmol) was used to afford 48 (60.2 mg, 3.1%) and 66 (1.6 g, 80.2%) as pale yellow powder.

2,3-Dihydro-2-(3',5'-dimethoxyphenyl)-4-quinazolinone (67). According to the preparation of 61 (Method B), 3,5-dimethoxybenzaldehyde (40) (1.2 g, 7.3 mmol) was used to afford 49 (40.2 mg, 2.0%) and 67 (1.9 g, 93.3%) as pale yellow powder.

2,3-Dihydro-2-(3'-methoxyphenyl)-6-chloro-4-quinazolinone (68). According to the preparation of 61 (Method B), 2-amino-5-chlorobenzamide (31) (1.0 g, 5.9 mmol) and 3-methoxybenzaldehyde (34) (0.8 g, 5.9 mmol) were used to afford 50 (20.0 mg, 1.1%) and 68 (1.6 g, 95.0%) as colorless powder.

4-Methoxy-2-phenylquinazoline (69) and $N^3$-methyl-2-phenyl-4-quinazolinone (77). Compound 41 (1.00 g, 4.50 mmol) was suspended in dry THF (50 ml), and NaH (80% in oil, 0.15 g, 5.00 mmol) was added portionwise with stirring for 60 min at 50° C. Methyl iodide (1.28 g, 9.00 mmol) was then added and stirred continuously for additional 60 min. The reaction mixture was dissolved in $CHCl_3$ and evaporated after removed the salts by filtration. The residue was purified by chromatography on silica gel. Elution with $CHCl_3$/hexane (2:1) yielded 69 (0.32 g, 30.1%) and 77 (0.70 g, 66.0%) as colorless powder. Yield, mp, and spectral data are given in Table 2.

4-Ethoxy-2-phenylquinazoline (70) and $N^3$-Ethyl-2-phenyl-4-quinazolinone (78). According to the preparation of 69 and 77, ethyl iodide (1.40 g, 9.00 mmol) was used to yield 70 (0.90 g, 80.0%) and 78 (0.12 g, 11.0%) as colorless powder.

4-Ethoxycarbonylmethoxy-2-phenylquinazoline (71) and $N^3$-Ethoxycarbonylmethoxy-2-phenyl-4-quinazolinone (79). According to the preparation of 69 and 77, ethyl bromoacetate (1.50 g, 9.00 mmol) was used to yield 71 (1.25 g, 90.2%) and 79 (0.02 g, 1.3%) as colorless powder.

4-Ethoxycarbonylpropoxy-2-phenylquinazoline (72). According to the preparation of 69, ethyl 4-chlorobutyrate (1.36 g, 9.00 mmol) was used to yield 72 (1.34 g, 88.6%) as colorless powder.

4-Ethoxycarbonylbutoxy-2-phenylquinazoline (73). According to the preparation of 69, ethyl 5-bromovalerate (1.88 g, 9.00 mmol) was used to yield 73 (1.25 g, 79.4%) as colorless powder.

4-Ethoxy-2-(2'-methoxyphenyl)quinazoline (74). According to the preparation of 69, 42 (1.13 g, 4.5 mmol) and ethyl iodide (1.40 g, 9.00 mmol) was used to yield 74 (1.06 g, 84.1%) as colorless powder.

4-Ethoxy-2-(3'-methoxyphenyl)quinazoline (75) and $N^3$-Ethyl-2-(3'-methoxyphenyl)-4-quinazolinone (80). According to the preparation of 69 and 77, 43 (1.13 g, 4.5 mmol) and ethyl iodide (1.40 g, 9.00 mmol) was used to yield 75 (1.04 g, 82.5%) and 80 (0.14 g, 11.1%) as colorless powder.

4-Ethoxy-2-(4'-methoxyphenyl)quinazoline (76) and $N^3$-Ethyl-2-(4'-methoxyphenyl)-4-quinazolinone (81). According to the preparation of 69 and 77, 44 (1.13 g, 4.5 mmol) and ethyl iodide (1.40 g, 9.00 mmol) was used to yield 76 (1.07 g, 85.0%) and 81 (0.11 g, 8.8%) as colorless powder.

B. Biological Assays a. Cytotoxicity assays. Compounds 42~68 were assayed for in vitro cytotoxicity in a panel of human and murine tumor cell lines at the School of Pharmacy, University of North Carolina at Chapel Hill, according to procedures described previously [Lee, K. H.; Lin, Y. M.; Wu, T. S.; Zhang, D. C.; Yamagishi, T.; Hayashi, T.; Hall, I. H.; Chang, J. J.; Wu, R. Y.; Yang, T. H. The cytotoxic principles of *Prunella vulgaris, Psychotria serpens, and Hyptis captitata*: Ursolic acid and related derivatives. *Planta Med.* 1988, 54, 308–312.] The cell lines include human ovarian cancer (1A9), ileocecal carcinoma (HCT-8), lung carcinoma (A-549), glioblastoma (U-87-MG), bone (HOS), epidermoid carcinoma of the nasopharynx (KB), P-gp-expressing epidermoid carcinoma of the nasopharynx (KB-VIN), prostate cancer (PC3), breast cancer (MCF-7), and melanoma (SKMEL-2) cell lines. The cytotoxic effects of each compound were obtained as $ED_{50}$ values, which represent the molar drug concentrations required to cause 50% inhibition.

b. Antimicrotubule assay. Electrophoretically homogeneous bovine brain tubulin was purified as described previously [Hamel, E.; Lin, C. M. Separation of active tubulin and microtubule-associated proteins by ultracentrifugation and isolation of a component causing the formation of microtubule bundles. *Biochemistry* 1984, 23, 4173–4184]. Combretastatin A-4 was a generous gift of Dr. G. R. Pettit, Arizona State University.

The tubulin polymerization assay was performed as described previously [D'Amato, R. J.; Lin, C. M.; Flynn, E.; Folkman, J.; Hamel, E. 2-Methoxyestradiol, an endogenous mammalian metabolite, inhibits tubulin polymerization by interacting at the colchicine site. *Proc. Natl. Acad. Sci. U.S.A.* 1994, 91, 3964–3968]. In brief, tubulin at 1.2 mg/ml (12 $\mu$M) was preincubated for 15 min at 26° C. in a 0.24-ml volume of 0.8 M monosodium glutamate (pH 6.6 with NaOH in a 2 M stock solution) with varying drug concentrations. The drug stock solutions were in DMSO, and the final solvent concentration was 4% (v/v). All concentrations are in terms of the final reaction volume (0.25 ml). The reaction mixtures were chilled on ice, and 10 $\mu$l of 10 mM GTP was added to each reaction mixture. Samples were transferred to cuvettes held at 0° C. by an electronic temperature controller in Gilford spectrophotometers. Baselines were established at 350 nm, and polymerization was initiated by a temperature jump to 26° C. The jump took about 50 s to complete. After 20 min, turbidity readings were recorded, and the temperature controller was set to 0° C. When depolymerization was complete, turbidity readings were again recorded. Generally, turbidity readings were about 90% cold-reversible and the cold-reversible turbidity was taken to represent the extent of assembly for each reaction mixture. $IC_{50}$ valued were obtained graphically from inhibition of polymerization by different drug concentrations. Four spectrophotometers were used for each experimental sequence, with two control reactions (no drug) in each set. Generally, the control reactions were within 5% of their average and $IC_{50}$ values obtained with this polymerization assay are usually highly reproducible. Generally, standard deviations were within 20% of the mean values, but in some cases, the standard deviations were 30–35% of the mean. Therefore, we can conservatively estimate that a 50% difference in $IC_{50}$ values represents a difference in the relative activity of two agents.

c. Antiplatelet assay. Blood, collected from the marginal ear vein of rabbits was mixed with EDTA to a final concentration of 6 mM and centrifuged at 90 g for 10 mm at room temperature to obtain platelet-rich plasma. The latter was further centrifuged at 500 g for 10 mm and the platelets were washed with Tyrode's solution without EDTA. After centrifugation at the same conditions, the platelets were suspended in Tyrode's solution with the following compositions (mM): NaCl (136.8), KCl (2.8), $NaNCO_3$(11.9), $MgCl_2$(1.1), $NaH_2PO_4$(0.33), $CaCl_2$(1.0), and glucose (11.2). Platelet numbers were determined with a Coulter Counter (Model ZM) and adjusted to $4.5 \times 10^8$ platelets/ml.

Aggregation was measured by the turbidimetric method [O'brien, J. R. J. Clin. Pathol. 1962, 15,452] with a dual-channel Lumi aggregometer (Model 1020, Payton, Canada). All glass ware was siliconized. Test compounds were added one minute before the addition of the aggregation inducer and the platelet suspension was stirred at 900 rpm. The percentage of aggregation was calculated as previously described [Teng, C. M.; Chen, W. Y.; Ko, W. C.; Ouyang, C. Biochem. Biophys. Acta. 1987, 924, 375].

RESULTS AND DISCUSSION a. Evaluation of Cytotoxicity of PQZ and DHPQZ Derivatives The 6,7,2',3',4',5'-substituted 2-phenyl-4-quinazolinones (42–59) and 6,2',3',4',5'-substituted 2,3-dihydro-2-phenyl-4-quinazolinones (60–68) were assayed for cytotoxicity in vitro against ten human tumor cell lines, including human ovarian cancer (1A9), ileocecal carcinoma (HCT-8), lung carcinoma (A-549), glioblastoma (U-87-MG), bone (HOS), epidermoid carcinoma of the nasopharynx (KB), P-gp-expressing epidermoid cacinoma of the nasopharynx (KB-VIN), prostate cancer (PC3), breast cancer (MCF-7), and melanoma (SKMEL-2) cell lines. As shown in Table 3, 55–58 showed strong cytotoxic effects towards a variety of tumor cell lines, with $ED_{50}$ values<1.0 $\mu$g/mL, but 55 was inactive in U-87-MG or HOS cell lines. Notably, 55–58 showed highly selective effects on ovarian cancer (1A9). For example, the $ED_{50}$ value of 55 in 1A9 was 0.49 $\mu$g/ml, and growth of cells from this more sensitive cell line was arrested at a concentration approximately 20–30 times lower than those in less sensitive cell lines (e.g. A-549, KB, PC3, and SKMEL-2). Similar high anti-ovarian cell selectivity was also found with 56–59. In addition, 55–58 displayed increased activity against the P-gp- expressing cell line KB-VIN relative to the parental cell line (KB), with 55 and 57 showing about 25 times and 15 times greater sensitivity to the drug resistant cell line. Although the structural difference between 55 and 56 is very small, 56 was significantly more cytotoxic; however, it showed reduced selectivity against KB-VIN. The reason is not clear, different mechanisms might be involved and mechanism studies are ongoing.

In terms of structure-activity relationships (SAR) information, PQZ derivatives (42–49) without C-6 substitutions were inactive. In comparing the effects of electron-donating or electron-withdrawing groups at the 6-position, the compound with an electron-donating methoxy (52) was more active than the electron withdrawing 6-Cl (50) or 6-F (51) PQZ derivatives. The (methylenendioxy)benzene moiety occurs commonly in many antimitotic agents, such as podophyllotoxin, steganacin, and combretastatin A-2. However, the 6,7-(methylenedioxy) substituted compound (54) did not show significant increased activity compared to either an unsubstitued (43), 6-methoxy (52), or 6,7-dimethoxy (53) compound. Single substitution at the 6-position seemed to be beneficial for increased antitumor activity; the 6-methoxy compound (52) was about 5-times more active than its corresponding 6,7-dimethoxy analog (53) in virtually all cell lines. Compounds with a heterocyclic ring or $N(CH_3)_2$ at the 6-position (55–59) displayed extremely high potency. Compound 56 with a 6-pyrrolidinyl ring was the most potent compound with $ED_{50}$ values in the nanomolar concentration range.

A fairly dramatic difference was observed between the PQZ (42–50) and DHPQZ (60–68) series. In the former group, little activity was observed with many cell lines. In contrast, in the latter group, highly selective activities were obtained against 1A9 and KB-Vin cell lines. Generally, DHPQZ derivatives showed greater activity than PQZ compounds with the same substitution. However, as the DHPQZ compounds tested in this study were all racemates, it is anreasonable to anticipate higher activity for one of the enantiomer pair. In terms of cytotoxicity in the more sensi tive cell lines, DHPQZ compounds with a methoxy at the 3-position (61) were about 15 or 20 times more active than 2'-methoxy (60), or 4'-methoxy (62) derivatives. In addition, 61 was also more active than multi-methoxy compounds (63–67). This result is consistant with observations in other heterocyclic ketones, such as PQ, DHPQ, and PN, as antimitotic antitumor agents. 6-C1-3'-methoxy DHPQZ (68) showed significantly increased cytotoxicity as compared to 61. The $ED_{50}$ of 68 was about 5-times less than that of 61.

As summarized in Table 3, the cytotoxic PQZ and DHPQZ compounds showed strong sensitivity in the ovarian cancer cell line, and were selective against drug-resistance KB cell line. These interesting results make PQZ and DHPQZ unique among structurally similar heterocyclic ketones, which were generally active against most human tumor cell lines in virtually all cases. The reasons for this selectivity and its modulation are not clear and will be investigated in future mechanism studies.

b. Interaction of PQZ and DHPQZ Derivatives with Tubulin

Previously, PQ, DHPQ, and PN derivatives were found to inhibit both tubulin polymerization and the binding of radiolabeled coichicine to tubulin. The chief structural differences between the PQ agents and the new PQZ series, as well as between DHPQ and the new DHPQZ series are the additional nitrogen atom in the B ring. The only structural difference between the two newly synthesized PQZ and DHPQZ compounds is the oxidation status of the bond between C(2) and N(3) in the B-ring. This modification results in configurational and conformational change in the relative positions of the aromatic rings A and C. Many studies have suggested that the interaction between colchicine and tubulin is stereoselective and is highly dependent on the conformation and configuration of the biaryl system formed by the trimethoxyphenyl A ring and tropolonic C ring. Thus, evaluation of the new agents for interactions with tubulin should provide additional insight into the mechanism of ligand binding at the colchicine site. In the previous paper [Xia, Y.; Yang, Z. Y.; Hour, M. J.; Kuo, S. C.; Xia, P.; Bastow, K. F.; Nakanishi, Y; Nampoothiri, P.; Hackl, T.; Hamel, E.; Lee, K. H. Synthesis and biological evaluation of substituted 2-arylquinazolinones. Bioorg. Med. Chem. Lett. (submitted)], selected molecules in the PQZ compounds were reported to be antimitotic agents inhibiting tubulin polymerization. To further delineate structure-activity relationships, the newly synthesized PQZ and DHPQZ compounds were evaluated as inhibitors of tubulin polymerization and compared with the classic antimitotic agents, colchicine, podophyllotoxin, and combretastatin A-4. The results are summarized in Table 4. Overall, the inhibitory effects on tubulin activities were in excellent agreement with the cytotoxicity data. The cytotoxic compounds (52, 55–57, 59, 68) all were substoichiometric inhibitors of tubulin polymerization, and the most cytotoxic compounds (56, 68) were also the most potent inhibitors of tubulin polymerization. These compounds had effects virtually identical to those of the natural products included for comparison. Conversely, the least cytotoxic compounds (42–51) had little or no inhibitory effect on tubulin polymerization.

As with the PQ, PN and DHPQ derivatives, PQZ and DHPQZ compounds without substitution at the A ring were less active than 6-substituted compounds. Compounds with 3'-methoxy (43, 61) substitution were more active than those with the same substituent at the 2'-(42, 60), or 4'-position (44, 62). Multi-methoxy compounds (45–49) showed decreased inhibitory activity in the tubulin assay, while 61–65 almost completely lost activity.

Compounds with a heterocyclic ring at the 6-position (56, 57, 59) were highly active, except for 58 ($IC_{50}$=10–20 $\mu$M) which has a 1-methyl-piperidinyl group at this position. The reason for the loss of activity in 58 is not clear; the relatively bulky size of this cyclic amine compared to other heterocyclic groups such as the pyrrolidinyl might be a factor. The 6-pyrrolidinyl DHPQZ compound (56) was the most active inhibitor of tubulin polymerization ($IC_{50}$<1 $\mu$M) in this study. It was almost equivalent to the antimitotic natural product colchicine. The corresponding noncyclic 6-(N,N-dimethylamino)-substituted compound (55) was also highly active ($IC_{50}$=1–4 $\mu$M).

Exceptions were found in the DHPQZ class of compounds. The equally cytotoxic compounds 62–66 were almost inactive ($IC_{50}$>40 $\mu$M) on tubulin polymerization. A possible reason is that the tested DHPQZ compounds were all racemates. Because protein-ligand interactions are almost always stereoselective, the lower antitubulin effects of 62–66 might be derived from the racemic mixtures. In our early studies, optically pure DHPQ derivatives showed significantly increased antitubulin activity compared with the racemates [Xia, Y.; Yang, Z. Y.; Hour, M. J.; Kuo, S. C.; Xia, P.; Bastow, K. F.; Nakanishi, Y; Nampoothiri, P.; Hackl, T.; Hamel, E.; Lee, K. H. Synthesis and biological evaluation of substituted 2-arylquinazolinones. Bioorg. Med. Chem. Lett. (submitted)]. herefore, it is still reasonable to anticipate that optically pure DHPQZ compounds could display potent antitubulin inhibition and the good correlationships between cytotoxicity and antitubulin effects remain uniformly consistant within these heterocyclic ketones. Also, optically pure 6-heterocyclic DHPQZ derivatives might well yield compounds with still greater potency and high antitumor selectivity.

c. Antiplatelet Activity

Table 5 tabulates the inhibitory effects of compounds 69 and 70 against platelet aggregation induced by four inducers consisting of thrombin, arachidonic acid (AA), collagen and platelet-activating factor (PAF). Both of them displayed very similar pattern of preferential inhibition. Namely, all of them are relatively stronger inhibitors against AA- and collagen-induced platelet aggregation, but are poor inhibitors for thrombin- and PAFinduced aggregation.

Table 6 shows the inhitory effects of compounds 69 to 79 on platelet aggregation induced by arachidonic acid (in vitro).

TABLE 1

Physical and Spectral Data of 6-Alkylamino-3'-methoxy-2-phenyl-4-quinazolinones, 2,3-Dihydro-3'-methoxy-2-phenyl-4-quinazolinones and Related Compounds

41–59

60–68

| compd | yield (%) | mp (° C.) | UV, λ$_{max}$ (MeOH) (log ε) | IR, ν$_{C=O}$ (cm$^{-1}$) | MS (M$^+$) m/z | $^1$H-NMR (DMSO-d$_6$) δ | analysis (%) calcd. (found) C | H | N |
|---|---|---|---|---|---|---|---|---|---|
| 41 | 93 | 232–233 | 237 (4.47) | 1671 | 222 | 7.48–7.59(4H, m, H-6, H-3', H-4', H-5'), 7.71–7.84(2H, m, H-7, H-8), 8.13–8.20(3H, m, H-5, H-2', H-6'), 12.56 (1H, br s, NH) | 75.66 (75.60) | 4.54 (4.46) | 12.61 (12.52) |
| 42 | 89 | 198–202 | 211 (4.50) | 1678 | 252 | 3.86(3H, s, OCH$_3$), 7.05–7.21(2H, m, H-3', H-5'), 7.49–7.58(2H, m, H-4', H-6), 7.69–7.73(2H, m, H-8), 7.83(1H, ddd, J=1.2, 8.0, 8.0Hz, H-7), 8.15(1H, dd, J=1.2, 8.0Hz, H-5), 12.13(1H, br s, NH) | 71.42 (71.40) | 4.80 (4.83) | 11.10 (11.12) |
| 43 | 95 | 177–179 | 218 (4.41) | 1672 | 252 | 3.86(3H, s, OCH$_3$), 7.14(1H, dd, J=2.2, 8.0Hz, H-4'), 7.41–7.56(2H, m, H-5', H-6), 7.74–7.88(4H, m, H-6', H-7, H-8), 8.15(1H, dd, J=1.2, 8.0Hz, H-5), 12.55(1H, br s, NH) | 71.42 (71.44) | 4.80 (4.78) | 11.10 (11.07) |
| 44 | 96 | 215–219 | 207 (4.38) | 1678 | 252 | 3.83(3H, s, OCH$_3$), 7.08 (2H, d, J=8.0Hz, H-3', H-5'), 7.47(1H, ddd, J=1.2, 8.0, 8.0Hz, H-6), 7.67-7.85(2H, m, H-7, H-8), 8.10-8.20(3H, m, H-2', H-6', H-5), 12.42 (1H, br s, NH) | 71.42 (71.39) | 4.80 (4.81) | 11.10 (11.13) |
| 45 | 86 | 179–181 | 223 (4.52) | 1678 | 282 | 3.76(3H, s, 2'-OCH$_3$ or 3'-OCH$_3$), 3.87(3H, s, 2'-OCH$_3$ or 3'-OCH$_3$), 7.18–7.28 (3H, m, H-4', H-5', H-6'), 7.54(1H, ddd, J=1.2, 8.0, 8.0Hz, H-6), 7.70(1H, dd, J=1.2, 8.0Hz, H-8), 7.84 (1H, ddd, J=1.2, 8.0, 8.0Hz, H-7), 8.16(1H, dd, J=1.2, 8.0Hz, H-5), 12.23(1H, br s, NH) | 68.08 (68.05) | 5.00 (5.06) | 9.92 (9.88) |
| 46 | 84 | 184–186 | 207 (4.27) | 1678 | 282 | 3.85(3H, s, 2'-OCH$_3$ or 4'-OCH$_3$), 3.89(3H, s, 2'-OCH$_3$ or 4'-OCH$_3$), 6.65–6.72(2H, m, H-3', H-5'), 7.49(1H, ddd, J=1.2, 8.0, 8.0Hz, H-6), 7.67(1H, dd, J=1.2, 8.0Hz, H-8), 7.76–7.85(2H, m, H-6', H-7), 8.12(1H, dd, J=1.2, 8.0 Hz, H-5), 11.82(1H, br s, NH) | 68.08 (68.13) | 5.00 (4.96) | 9.92 (9.86) |
| 47 | 88 | 143–144 | 220 (4.70) | 1698 | 282 | 3.77(3H, s, 2'-OCH$_3$ or 5'-OCH$_3$), 3.81(3H, s, 2'-OCH$_3$ or 5'-OCH$_3$), 7.10–7.12 (2H, m, H-3', H-4'), 7.29–7.31(1H, m, H-6'), 7.53 (1H, ddd, J=1.2, 8.0, 8.0Hz, H-6), 7.71(1H, dd, J=1.2, 8.0Hz, H-8), 7.83(1H, ddd, | 68.08 (68.00) | 5.00 (4.95) | 9.92 (9.97) |

TABLE 1-continued

| | | | | | | | | | |
|---|---|---|---|---|---|---|---|---|---|
| | | | | | | J=1.2, 8.0, 8.0Hz, H-7), 8.14(1H, dd, J=1.2, 8.0 Hz, H-5), 12.10(1H, br s, NH) | | | |
| 48 | 89 | 240–242 | 226 (4.44) | 1671 | 282 | 3.84(3H, s, 3'-OCH$_3$ or 4'-OCH$_3$), 3.88(3H, s, 3'-OCH$_3$ or 4'-OCH$_3$), 7.10 (1H, d, J=8.0Hz, H-5'), 7.48 (1H, ddd, J=1.2, 8.0, 8.0 Hz, H-6), 7.69–7.89(4H, m, H-2', H-6', H-7, H-8), 8.13 (1H, dd, J=1.2, 8.0Hz, H-5), 12.44(1H, br s, NH) | 68.08 (67.99) | 5.00 (5.03) | 9.92 (9.89) |
| 49 | 84 | 200–203 | 221 (4.57) | 1674 | 282 | 3.83(6H, s, 3'-OCH$_3$, 5'-OCH$_3$), 6.69(1H, dd, J=2.2, 2.2Hz, H-4'), 7.38(2H, d, J=2.2Hz, H-2', H-6'), 7.52(1H, ddd, J=1.2, 8.0, 8.0Hz, H-6), 7.74(1H, dd, J=1.2, 8.0Hz, H-8), 7.83 (1H, ddd, J=1.2, 8.0, 8.0Hz, H-7), 8.15(1H, dd, J=1.2, 8.0Hz, H-5), 12.52(1H, br s, NH) | 68.08 (68.11) | 5.00 (5.06) | 9.92 (9.85) |
| 50 | 94 | 245–248 | 218 (4.60) | 1678 | 286.5 | 3.86(3H, s, 3'-OCH$_3$), 7.16 (1H, dd, J=2.5, 8.0Hz, H-4'), 7.46(1H, dd, J=8.0, 8.0Hz, H-5'), 7.73–7.80 (3H, m, H-2', H-6', H-8), 7.87 (1H, dd, J=2.5, 8.0Hz, H-7), 8.09(1H, d, J=2.5Hz, H-5), 12.70(1H, br s, NH) | 62.84 (62.78) | 3.87 (3.80) | 9.77 (9.81) |
| 51 | 46.8 | 246–247 | 217 (4.70) | 1680 | 270 | 3.84(3H, s, 3'-OCH$_3$), 7.13 (1H, dd, J=2.5, 8.0Hz, H-4'), 7.44(1H, dd, J=8.0, 8.0 Hz, H-5'), 7.68–7.84(5H, m, H-2', H-6', H-5, H-7, H-8), 12.61(1H, br s, NH) | 66.66 (66.68) | 4.10 (4.08) | 10.37 (10.41) |
| 52 | 42 | 216–218 | 218 (4.69) | 1659 | 282 | 3.86(3H, s, 3'-OCH$_3$ or 6-OCH$_3$), 3.96(3H, s, 3'-OCH$_3$ or 6-OCH$_3$), 7.11(1H, dd, J=2.5, 8.0Hz, H-4'), 7.29–7.49(2H, m, H-5', H-7), 7.53(1H, d, J=2.5Hz, H-5), 7.67–7.82(3H, m, H-6', H-8), 12.48(1H, br s, NH) | 68.08 (68.04) | 5.00 (5.06) | 9.92 (9.86) |
| 53 | 30 | 266–267 | 253 (4.55) | 1658 | 312 | 3.86(3H, s, 3'-OCH$_3$ or 6-OCH$_3$ or 7-OCH$_3$), 3.89 (3H, s, 3'-OCH$_3$ or 6-OCH$_3$ or 7-OCH$_3$), 3.94(3H, s, OCH$_3$ or 6-OCH$_3$ or 7-OCH$_3$), 7.11(1H, dd, J=1.2, 8.0Hz, H-4'), 7.21(1H, s, H-8), 7.43(1H, dd, J=8.0 8.0Hz, H-5'), 7.48(1H, s, H-5), 7.73–7.78(2H, m, H-2', H-6'), 12.40(1H, br s, NH) | 65.38 (65.30) | 5.16 (5.20) | 8.97 (8.91) |
| 54 | 8.8 | 269–270 | 249 (4.48) | 1665 | 296 | 3.85(3H, s, 3'-OCH$_3$), 6.20 (2H, s, OCH$_2$O), 7.11(1H, dd, J=2.2, 8.0Hz, H-4'), 7.18(1H, s, H-8), 7.43(1H, dd, J=8.0, 8.0Hz, H-5'), 7.44(1H, s, H-5), 7.68–7.75 (2H, m, H-2', H-6'), 12.46 (1H, br s, NH) | 64.86 (64.89) | 4.08 (4.03) | 9.46 (9.50) |
| 55 | 51 | 239–241 | 224 (4.79) | 1659 | 295 | 3.01(s, 6H, N(CH$_3$)$_2$), 3.85 (3H, s, 3'-OCH$_3$), 7.07(1H, dd, J=2.5, 8.0Hz, H4'), 7.21(1H, d, J=2.5Hz, H-5), 7.33(1H, dd, J=2.5, 8.0 Hz, H-7), 7.41(1H, dd, J=8.0, 8.0Hz, H-5'), 7.61(1H, d, J=8.0Hz, H-8), 7.70–7.76 (2H, m, H-2', H-6'), 12.26 (1H, br s, NH) | 69.14 (69.10) | 5.80 (5.77) | 14.23 (14.20) |
| 56 | 40 | 261–263 | 227 (4.54) | 1653 | 321 | 1.96–2.03(4H, m, CH$_2$CH$_2$NCH$_2$CH$_2$), 3.30– | 71.01 (71.05) | 5.96 (5.90) | 13.08 (13.02) |

TABLE 1-continued

| | | | | | | | | |
|---|---|---|---|---|---|---|---|---|
| | | | | | | 3.34(4H, m, CH$_2$NCH$_2$), 3.85(3H, s, 3'-OCH$_3$), 7.03–7.17(3H, m, H-4', H-5, H-7), 7.41(1H, dd, J=8.0, 8.0 Hz, H-5'), 7.60(1H, d, J=8.0Hz, H-8), 7.68–7.75(2H, m, H-2', H-6'), 12.22(1H, br s, NH) | | |
| 57 | 55 | 222–225 | 1668 (4.71) | 335 | 1.55–1.60(6H, m, (CH$_2$)$_2$CH$_2$NCH$_2$CH$_2$), 3.25–3.30(4H, m, CH$_2$NCH$_2$), 3.85(3H, s, 3'-OCH$_3$), 7.09(1H, dd, J=2.2, 8.0Hz, H-4'), 7.38–7.46(2H, m, H-5), 7.53(1H, dd, J=2.2, 8.0Hz, H-7), 7.60(1H, d, J=8.0Hz, H-8), 7.70–7.76(2H, m, H-2', H-6'), 12.33(1H, br s, NH) | 71.62 (71.59) | 6.31 (6.28) | 12.53 (12.50) |
| 58 | 57 | 212–215 | 1663 (4.61) | 349 | 0.93(3H, d, J=6.2Hz, CH$_3$CH(CH$_2$)$_2$N(CH$_2$)$_2$), 1.20–1.26, 1.68–1.74(2H each, both m, (NCH$_2$CH$_2$) × 2), 1.48–1.58(1H, m, CH$_3$CH(CH$_2$)$_2$N(CH$_2$)$_2$, 2.71–2.82, 3.75–3.83(2H each, both m, (NCH$_2$) × 2), 3.85(3H, s, 3'-OCH$_3$), 7.09(1H, dd, J=2.2, 8.0Hz, H-4'), 7.38–7.46(2H, m, H-5), 7.54(1H, dd, J=2.2, 8.0Hz, H-7), 7.61(1H, d, J=8.0Hz, H-8), 7.71–7.77(2H, m, H-2', H-6'), 12.34(1H, br s, NH) | 72.18 (72.15) | 6.63 (6.60) | 12.03 (12.09) |
| 59 | 48 | 254–257 | 1673 (4.66) | 337 | 3.23(4H, t, J=4.7Hz, CH$_2$NCH$_2$), 3.75(4H, t, J=4.7Hz, CH$_2$OCH$_2$), 3.85(3H, s, 3'-OCH$_3$), 7.10(1H, dd, J=2.5, 8.0Hz, H4'), 7.43(1H, dd, J=8.0, 8.0 Hz, H-5'), 7.45(1H, d, J=2.5Hz, H-5), 7.57(1H, dd, J=2.5, 8.0Hz, H-7), 7.65(1H, d, J=8.0Hz, H-8), 7.71–7.77(2H, m, H-2', H-6'), 12.39(1H, br s, NH) | 67.64 (67.61) | 5.68 (5.70) | 12.46 (12.50) |
| 60 | 90 | 163–165 | 1668 (4.54) | 254 | 3.83(3H, s, OCH$_3$), 6.02(1H, s, H-2), 6.66(1H, dd, J=7.5, 7.5Hz, H-6), 6.74–6.80(2H, m, H-8, N$_1$H), 6.94(1H, dd, J=7.5, 7.5Hz, H-5'), 7.04(1H, d, J=8.0Hz, H-3'), 7.18–7.41(3H, m, H-4', H-6', H-7), 7.62(1H, dd, J=1.0, 1.0Hz, H-5), 8.02(1H, br s, N$_3$H) | 70.85 (70.91) | 5.55 (5.53) | 11.02 (11.10) |
| 61 | 89 | 148–150 | 1647 (4.50) | 254 | 3.73(3H, s, OCH$_3$), 5.73(1H, s, H-2), 6.68(1H, dd, J=7.5, 7.5Hz, H-6), 6.77(1H, d, J=8.0Hz, H-8), 6.90(1H, dd, J=8.0, 2.5Hz, H-4'), 7.04–7.07(2H, m, H-2', H-6'), 7.15(1H, br s, N$_1$H), 7.21–7.33(2H, m, H-5', H-7), 8.15(1H, dd, J=1.0, 7.5 Hz, H-5), 8.34(1H, br s, N$_3$H) | 70.85 (70.81) | 5.55 (5.49) | 11.02 (11.08) |
| 62 | 93 | 188–190 | 1655 (4.64) | 254 | 3.73(3H, s, OCH$_3$), 5.70(1H, s, H-2), 6.67–6.75(2H, m, H-6, H-8), 6.91–6.95(2H, m, H-3', H-5'), 7.00(1H, br s, N$_1$H), 7.24(1H, ddd, J= | 70.85 (70.79) | 5.55 (5.59) | 11.02 (10.95) |

TABLE 1-continued

| | | | | | | | | | |
|---|---|---|---|---|---|---|---|---|---|
| | | | | | | 1.5, 8.0, 8.0Hz, H-7), 7.36–7.62(2H, m, H-2', H-6'), 7.60(1H, dd, J=1.2, 7.5 Hz, H-5), 8.19(1H, br s, N$_3$H) | | | |
| 63 | 78 | 232–233 | 224 (4.54) | 1651 | 284 | 3.78(3H, s, 2'-OCH$_3$ or 3'-OCH$_3$), 3.81(3H, s, 2'-OCH$_3$ or 3'-OCH$_3$), 6.03 (1H, s, H-2), 6.63–6.75(2H, m, H-6, H-8), 6.79(1H, br s, N$_1$H), 7.04–7.10(3H, m, H-4', H-5', H-6'), 7.23(1H, ddd, J=1.0, 8.0, 8.0Hz, H-7), 7.62(1H, dd, J=1.0, 8.0 Hz, H-5), 8.02(1H, br s, N$_3$H) | 67.59 (67.55) | 5.67 (5.71) | 9.85 (9.80) |
| 64 | 86 | 182–183 | 225 (4.45) | 1663 | 284 | 3.75(3H, s, 2'-OCH$_3$ or 4'-OCH$_3$), 3.81(3H, s, 2'-OCH$_3$ or 4'-OCH$_3$), 5.94 (1H, s, H-2), 6.49–6.77(5H, m, H-3', H-5', H-6, H-8, N$_1$H ), 7.21(1H, ddd, J=1.0, 8.0, 8.0Hz, H-7), 7.31 (1H, d, J=8.0, H-6'), 7.61 (1H, dd, J=1.0, 7.5Hz, H-5), 7.94(1H, br s, N$_3$H) | 67.59 (67.53) | 5.67 (5.63) | 9.85 (9.81) |
| 65 | 75 | 163–165 | 223 (4.53) | 1653 | 284 | 3.66(3H, s, 2'-OCH$_3$ or 5'-OCH$_3$), 3.78(3H, s, 2'-OCH$_3$ or 5'-OCH$_3$), 5.98 (1H, s, H-2), 6.68(1H, dd, J=7.5, 7.5Hz, H-6), 6.77(1H, d, J=8.0Hz, H-8), 6.84–7.00 (4H, m, H-3', H-4', H-6', N$_1$H), 7.23(1H, ddd, J=1.0, 8.0, 8.0Hz, H-7), 7.63(1H, dd, J=1.0, 7.5Hz, H-5), 8.02(1H, br s, N$_3$H) | 67.59 (67.54) | 5.67 (5.70) | 9.85 (9.88) |
| 66 | 80 | 210–213 | 223 (4.61) | 1655 | 284 | 3.73(3H, s, 3'-OCH$_3$ or 4'-OCH$_3$), 3.74(3H, s, 3'-OCH$_3$ or 4'-OCH$_3$), 5.70 (1H, s, H-2), 6.66(1H, dd, J=7.5, 7.5Hz, H-6), 6.75(1H, d, J=7.5Hz, H-8), 6.91–7.02 (3H, m, H-2', H-5', H-6'), 7.12(1H, br s, NH), 7.25 (1H, ddd, J=1.0, 7.5, 7.5Hz, H-7), 7.61(1H, dd, J=1.0, 7.5Hz, H-5), 8.19(1H, br s, N$_3$H) | 67.59 (67.51) | 5.67 (5.70) | 9.85 (9.78) |
| 67 | 93 | 89–92 | 223 (4.54) | 1658 | 284 | 3.72(6H, s, 3'-OCH3, 5' OCH$_3$), 5.67(1H, s, H-2), 6.46(1H, s, H-4'), 6.64–6.77 (4H, m, H-2', H-6', H-6, H-8), 7.13(1H, br s, N$_1$H), 7.24(1H, ddd, J=1.0, 7.5, 7.5Hz, H-7), 7.60(1H, dd, J=1.0, 7.5Hz, H-5), 8.30 (1H, br s, N$_3$H) | 67.59 (67.63) | 5.67 (5.66) | 9.85 (9.88) |
| 68 | 95 | 193–195 | 223 (4.57) | 1658 | 288.5 | 3.74(3H, s, OCH$_3$), 5.75 (1H, s, H-2), 6.79(1H, d, J=8.0Hz, H-8), 6.92(1H, dd, J=2.5, 8.0Hz, H-4'), 7.02–7.05(2H, m, H-2', H-6'), 7.25–7.36(3H, m, H-5', H-7, N$_1$H), 7.53(1H, d, J=2.5 Hz, H-5), 8.50(1H, br s, N$_3$H) | 62.40 (62.48) | 4.54 (4.50) | 9.70 (9.78) |

TABLE 2

Physical and Spectral Data of 4-Alkoxy-2-phenyl-4-quinazolines and N-Alkyl-2-phenyl-4-quinazolinones

69–76 / 77–81

| compd | yield (%) | mp (° C.) | UV, $\lambda_{max}$ (MeOH) (log ε) | IR, $\nu_{C=O}$ (cm$^{-1}$) | MS (M$^+$) m/z | $^1$H-NMR (CDCl$_3$) δ | analysis (%) calcd. (found) C | H | N |
|---|---|---|---|---|---|---|---|---|---|
| 69 | 30 | 50–51 | 254 (4.50) | | 236 | 4.26(3H, s, CH$_3$), 7.45–7.54 (4H, m, H-6, H-3', H4', H-5'), 7.79(1H, ddd, J=1.2, 8.0, 8.0Hz, H-7), 7.98(1H, dd, J=1.2, 8.0Hz, H-8), 8.13(1H, dd, J=1.2, 8.0 Hz, H-5), 8.57–8.62(2H, m, H-2', H-6') | 76.25 (76.33) | 5.12 (4.99) | 11.86 (11.72) |
| 70 | 80 | 54–56 | 255 (4.53) | | 250 | 1.56(3H, t, J=7.0Hz, CH$_3$), 4.76(2H, q, J=7.0 Hz, CH$_2$), 7.45–7.53(4H, m, H-6, H-3', H-4', H-5'), 7.79 (1H, ddd, J=1.2, 8.0, 8.0 Hz, H-7), 7.97(1H, dd, J=1.2, 8.0Hz, H-8), 8.16(1H, dd, J=1.2, 8.0Hz, H-5), 8.54–8.59(2H, m, H-2', H-6') | 76.78 (76.64) | 5.64 (5.68) | 11.19 (11.09) |
| 71 | 90 | 64–65 | 256 (4.52) | 1763 | 308 | 1.26(3H, t, J=7.0Hz, CH$_3$), 4.26(2H, q, J=7.0 Hz, CH$_2$CH$_3$), 5.16(2H, s, OCH$_2$CO), 7.46–7.57(4H, m, H-6, H-3', H-4', H-5'), 7.82(1H, ddd, J=1.2, 8.0, 8.0Hz, H-7), 8.00(1H, dd, J=1.2, 8.0Hz, H-8), 8.23(1H, dd, J=1.2, 8.0Hz, H-5), 8.48–8.53(2H, m, H-2', H-6') | 70.12 (70.29) | 5.23 (5.31) | 9.09 (9.13) |
| 72 | 89 | 63–66 | 254 (4.46) | 1728 | 336 | 1.22(3H, t, J=7.0Hz, CH$_3$), 2.25–2.32(2H, m, OCH$_2$CH$_2$CH$_2$CO), 2.62 (2H, t, J=7.0Hz, OCH$_2$CH$_2$CH$_2$CO), 4.12 (2H, q, J=7.0Hz, CH$_2$CH$_3$), 4.75(2H, t, J=7.0Hz, OCH$_2$CH$_2$CH$_2$CO), 7.43–7.55 (4H, m, H-6, H-3', H4', H-5'), 7.79(1H, ddd, J=1.2, 8.0, 8.0Hz, H-7), 7.97(1H, dd, J=1.2, 8.0Hz, H-8), 8.13(1H, dd, J=1.2, 8.0 Hz, H-5), 8.51–8.58(2H, m, H-2', H-6') | 71.41 (71.35) | 5.99 (5.86) | 8.33 (8.28) |
| 73 | 79 | 62–63 | 254 (4.62) | 1728 | 350 | 1.24(3H, t, J=7.0Hz, CH$_3$), 1.90–1.99(4H, m, OCH$_2$(CH$_2$)$_2$CH$_2$CO), 2.44(2H, t, J=7.0Hz, O(CH$_2$)$_3$CH$_2$CO), 4.12 (2H, q, J=7.0Hz, CH$_2$CH$_3$), 4.72(2H, t, J=7.0Hz, OCH$_2$(CH$_2$)$_3$CO), 7.45–7.53 (4H, m, H-6, H-3', H4', H-5'), 7.79(1H, ddd, J=1.2, 8.0, 8.0Hz, H-7), 7.97(1H, dd, J=1.2, 8.0Hz, H-8), 8.15(1H, dd, J=1.2, 8.0 Hz, H-5), 8.53–8.58(2H, m, H-2', H-6') | 71.98 (71.86) | 6.33 (6.39) | 7.99 (7.92) |
| 74 | 84 | 154–155 | 210 (4.54) | | 280 | 1.11(3H, t, J=7.0Hz, CH$_2$CH$_3$), 3.63(1H, m, J= | 72.84 (72.80) | 5.75 (5.82) | 9.99 (9.97) |

TABLE 2-continued

| | | | | | | 7.0Hz, CH$_2$), 3.79(3H, s, OCH$_3$), 4.22(1H, m, J=7.0 Hz, CH$_2$), 6.99(1H, d, J= 8.0Hz, H-3'), 7.08(1H, ddd, J=1.2, 8.0, 8.0Hz, H-6), 7.44–7.54(3H, m, H-7, H-8, H-5'), 7.73(2H, m, H-4', H-6'), 8.32(1H, dd, J=1.2, 8.0 Hz, H-5) | | | |
|---|---|---|---|---|---|---|---|---|---|
| 75 | 83 | 85–86 | 213 (4.53) | | 280 | 1.55(3H, t, J=7.0Hz, CH$_2$CH$_3$), 3.92(3H, s, OCH$_3$), 4.75(2H, q, J=7.0 Hz, CH$_2$), 7.03(1H, ddd, J= 1.2, 1.2, 8.0Hz, H-6'), 7.40 (1H, dd, J=8.0, 8.0Hz, H-5'), 7.49(1H, ddd, J=1.2, 8.0, 8.0Hz, H-6), 7.79(1H, ddd, J=1.2, 8.0, 8.0Hz, H-7), 7.97(1H, dd, J=1.0, 8.0 Hz, H-8), 8.13–8.20(3H, m, H-5, H-2', H-4') | 72.84 (72.78) | 5.75 (5.89) | 9.99 (9.91) |
| 76 | 85 | 65–66 | 211 (4.54) | | 280 | 1.54(3H, t, J=7.0Hz, CH$_2$CH$_3$), 3.87(3H, s, OCH$_3$), 4.74(2H, q, J=7.0 Hz, CH$_2$), 7.00(2H, d, J= 8.0Hz, H-3', H-5'), 7.44(1H, ddd, J=1.2, 8.0, 8.0Hz, H-6), 7.76(1H, ddd, J=1.2, 8.0, 8.0Hz, H-7), 7.92(1H, dd, J=1.2, 8.0Hz, H-8), 8.12(1H, dd, J=1.2, 8.0 Hz, H-5), 8.53(2H, d, J= 8.0Hz, H-2', H-4') | 72.84 (72.89) | 5.75 (5.67) | 9.99 (9.87) |
| 77 | 66 | 125–127 | 229 (4.52) | 1682 | 236 | 3.47(3H, s, CH$_3$), 7.47–7.56 (6H, m, H-6, H-2', H-3', H-4, H-5', H-6'), 7.71–7.74 (2H, m, H-7, H-8), 8.30(1H, dd, J=1.2, 8.0Hz, H-5) | 76.25 (76.10) | 5.12 (5.20) | 11.86 (11.72) |
| 78 | 11 | 111–113 | 207 (4.43) | 1675 | 250 | 1.19(3H, t, J=7.0Hz, CH$_3$), 4.01(2H, q, J=7.0 Hz, CH$_2$), 7.47–7.51(6H, m, H-6, H-2', H-3', H-4', H-5' H-6'), 7.70–7.74(2H, m, H-7, H-8), 8.31(1H, dd, J= 1.2, 8.0Hz, H-5) | 76.78 (76.89) | 5.64 (5.70) | 11.19 (11.23) |
| 79 | 1.3 | 130–132 | 226 (4.67) | 1682 | 308 | 1.23(3H, t, J=7.0Hz, CH$_3$), 4.19(2H, q, J=7.0 Hz, CH$_2$CH$_3$), 4.62(2H, s, NCH$_2$), 7.46–7.57(6H, m, H-6, H-2', H-3', H-4', H-5' H-6'), 7.75–7.78(2H, m, H-7, H-8), 8.30(1H, dd, J= 1.2, 8.0Hz, H-5) | 70.12 (70.04) | 5.23 (5.33) | 9.09 (9.00) |
| 80 | 11 | 79–82 | 223 (4.51) | 1686 | 280 | 1.21(3H, t, J=7.0Hz, CH$_2$CH$_3$), 3.84(3H, s, OCH$_3$), 4.02(2H, q, J=7.0 Hz, CH$_2$), 7.00–7.10(3H, m, H-2', H-4', H-6'), 7.37–7.52 (2H, m, H-6, H-5'), 7.68–7.74(2H, m, H-7, H-8), 8.31 (1H, dd, J=1.2, 8.0Hz, H-5) | 72.84 (72.79) | 5.75 (5.86) | 9.99 (9.87) |
| 81 | 8.8 | 131–134 | 226 (4.55) | 1674 | 280 | 1.19(3H, t, J=7.0Hz, CH$_2$CH$_3$), 3.85(3H, s, OCH$_3$), 4.05(2H, q, J=7.0 Hz, CH$_2$), 7.00(2H, J=8.0 Hz, H-3', H-5'), 7.42–7.51 (3H, m, H-6, H-2', H-6'), 7.66–7.77(2H, m, H-7, H-8), 8.29 (1H, dd, J=1.2, 8.0Hz, H-5) | 72.84 (72.80) | 5.75 (5.77) | 9.99 (9.92) |

TABLE 3

In Vitro Cytotoxicity of 6,7,2',3',4',5'-Substituted 2-phenyl-4-quinazolinones (42–59) and 6,2',3',4',5'-Substituted 2,3-dihydro-2-phenyl-4-quinazolinones (60–68)

$ED_{50}(\mu g/ml)^a$

| compd | 1A9[b] | HCT-8[b] | A-549[b] | U-87-MG[b] | HOS | KB[b] | KB-VIN[b] | PC3[b] | MCF-7[b] | SKMEL-2 |
|---|---|---|---|---|---|---|---|---|---|---|
| 42 | >20(8)[c] | NA | >20(15) | NA | >20(5) | >20(6) | >20(9) | NA | >20(23) | NA |
| 43 | >20(27) | >20(8) | >20(21) | NA | >20(6) | NA | >20(12) | >20(16) | 26 | >20(12) |
| 44 | >20(22) | >20(29) | >20(42) | NA | >20(21) | >20(23) | >20(40) | >20(32) | >20(42) | >20(24) |
| 45 | NA | NA | >20(19) | NA | NA | NA | >20(11) | >20(17) | >20(24) | NA |
| 46 | NA | >20(14) | >20(31) | >20(16) | >20(7) | >20(5) | >20(8) | >20(16) | >20(15) | >20(5) |
| 47 | >20(19) | >20(21) | >20(33) | NA | >20(20) | >20(10) | >20(21) | >20(30) | >20(20) | >20(9) |
| 48 | >20(34) | >20(15) | >20(29) | NA | >20(11) | >20(12) | >20(22) | >20(26) | >20(48) | >20(15) |
| 49 | NA | NA | >20(29) | NA | NA | NA | >20(12) | >20(8) | >20(28) | >20(5) |
| 50 | >20(29) | 6.0 | 3.2 | 10.0 | 17.0 | 11.5 | 6.5 | 4.5 | 17.8 | 4.8 |
| 51 | NA | >20(31) | 16.5 | >20(30) | NA | >20(39) | 18.0 | 20.0 | >20(40) | >20(41) |
| 52 | 3.4 | 16.5 | 12.5 | >20(11) | >20(43) | 17.5 | 3.5 | >20(37) | 8.0 | >20(49) |
| 53 | 16.5 | >20(37) | >20(49) | >20(28) | >20(27) | >20(45) | 19.8 | 15.0 | 12.0 | 18.0 |
| 54 | >20(26) | NA | >20(11) | NA | >20(6) | >20(16) | >20(19) | >20(12) | >20(40) | >20(14) |
| 55 | 0.49 | 1.05 | 14.0 | >20(17) | >20(46) | 10.0 | 0.42 | 15.0 | 0.85 | 19.0 |
| 56 | 0.09 | 0.06 | 0.50 | 13.8 | 7.0 | 0.23 | 0.10 | 15.0 | 0.22 | 0.09 |
| 57 | 0.90 | 4.3 | 2.8 | 9.0 | 15.4 | 10 | 0.60 | 10.0 | 8.5 | 4.5 |
| 58 | 0.80 | 4.0 | 6.0 | 15.5 | 14.4 | 10.8 | 2.5 | 12.4 | 10.0 | 7.5 |
| 59 | 3.8 | 10.4 | 10.9 | 20 | 12.5 | 8.2 | 3.7 | 13.4 | 4.5 | 4.8 |
| 60 | 14.7 | >20(21) | >20(44) | NA | >20(38) | >20(32) | 10.2 | >20(30) | >20(48) | <20(52)[d] |
| 61 | 1.0 | 1.5 | 3.0 | >20(35) | >20(42) | 3.0 | 1.20 | >20(43) | >20(48) | >20(49) |
| 62 | 20 | >20(19) | >20(34) | NA | >20(13) | >20(14) | >20(39) | >20(14) | >20(44) | >20(23) |
| 63 | 11.4 | >20(39) | >20(39) | NA | >20(34) | >20(41) | 8.6 | >20(20) | >20(40) | <20(53) |
| 64 | 12.5 | >20(29) | >20(43) | NA | >20(40) | >20(43) | 7.6 | >20(28) | >20(44) | >20(37) |
| 65 | 10.0 | >20(32) | >20(42) | >20(5) | >20(40) | >20(40) | 8.4 | >20(22) | >20(42) | >20(44) |
| 66 | 14.6 | >20(25) | >20(41) | NA | >20(24) | >20(28) | 16.0 | >20(30) | 20 | >20(24) |
| 67 | 1.92 | 3.0 | 5.0 | >20(37) | >20(41) | 4.7 | 1.6 | >20(44) | >20(49) | 4.4 |
| 68 | 0.27 | 0.48 | 0.6 | >20(37) | 20.0 | 0.95 | 0.42 | 2.5 | 16.0 | <2.5(56) |

[a]$ED_{50}$ was the concentration of compound which affords 50% reduction in cell number after 3–4 days incubation.
[b]Human ovarian cancer (1A9), ileocecal carcinoma (HCT-8), lung carcinoma (A-549), glioblastoma (U-87-MG), bone (HOS), epidermoid carcinoma of the nasopharynx (KB), P-gp-expressing epidermoid carcinoma of the nasopharynx (KB-VIN), prostate cancer (PC3), breast cancer (MCF-7), and melanoma (SKMEL-2) cell lines.
[c]Inhibition of 50 percent at highest test concentration (percent observed is given in brackets).
[d]Plateau-dose response apparent-Max. Inhibition of 50% seen at low dose but plateaus over broad dose range (range indicated with inhibition values given in brackets).

TABLE 4

Antitubulin Effects of 6,7,2',3',4',5'-Substituted 2-phenyl-4-quinazolinones(42–59) and 6,2',3',4',5'-Substituted 2,3-dihydro-2-phenyl-4-quinazolinones(60–68)

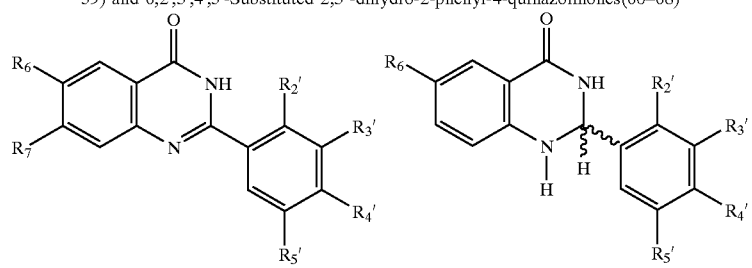

42–59         60–68

| compound | $R_6$ | $R_7$ | $R_{2'}$ | $R_{3'}$ | $R_{4'}$ | $R_{5'}$ | ITP[a] $IC_{50}(\mu M)$ |
|---|---|---|---|---|---|---|---|
| 42 | H | H | H | $OCH_3$ | H | H | 17 ± 1 |
| 43 | H | H | H | H | $OCH_3$ | H | 12 ± 1 |
| 44 | H | H | H | H | H | $OCH_3$ | 12 ± 2 |
| 45 | H | H | H | $OCH_3$ | $OCH_3$ | H | 15 ± 0.07 |
| 46 | H | H | H | $OCH_3$ | H | $OCH_3$ | 10 ± 0.4 |
| 47 | H | H | H | $OCH_3$ | H | H | $OCH_3$ |
| 48 | H | H | H | H | $OCH_3$ | $OCH_3$ | H | 15 ± 2 |
| 49 | H | H | H | H | $OCH_3$ | H | $OCH_3$ | 11 ± 2 |
| 50 | Cl | H | H | $OCH_3$ | H | H | 12 ± 0.9 |
| 51 | F | H | H | $OCH_3$ | H | H | 14 ± 2 |
| 52 | $OCH_3$ | H | H | $OCH_3$ | H | H | 6.7 ± 0.08 |
| 53 | $OCH_3$ | $OCH_3$ | H | $OCH_3$ | H | H | 9.1 ± 0.9 |
| 54 | $OCH_2O$ | | H | $OCH_3$ | H | H | 9.6 ± 0.6 |

TABLE 4-continued

Antitubulin Effects of 6,7,2',3',4',5'-Substituted 2-phenyl-4-quinazolinones(42–59) and 6,2',3',4',5'-Substituted 2,3-dihydro-2-phenyl-4-quinazolinones(60–68)

42–59

| compound | $R_6$ | $R_7$ | $R_{2'}$ | $R_{3'}$ | $R_{4'}$ | $R_{5'}$ | ITP[a] $IC_{50}(\mu M)$ |
|---|---|---|---|---|---|---|---|
| 55 | N(CH$_3$)$_2$ | H | H | OCH$_3$ | H | H | 3.5 ± 0.3 |
| 56 | pyrrolidinyl | H | H | OCH$_3$ | H | H | 1.1 ± 0.02 |
| 57 | piperidinyl | H | H | OCH$_3$ | H | H | 9.3 ± 2 |
| 58 | 4-methylpiperidinyl | H | H | OCH$_3$ | H | H | 12 ± 0.3 |
| 59 | morpholinyl | H | H | OCH$_3$ | H | H | 4.4 ± 0.1 |
| 60 | H | H | H | OCH$_3$ | H | H | >40 |
| 61 | H | H | H | H | OCH$_3$ | H | 5.6 ± 1 |
| 62 | H | H | H | H | OCH$_3$ | H | >40 |
| 63 | H | H | OCH$_3$ | OCH$_3$ | H | H | >40 |
| 64 | H | H | OCH$_3$ | H | OCH$_3$ | H | >40 |
| 65 | H | H | OCH$_3$ | H | H | OCH$_3$ | 32 ± 4 |
| 66 | H | H | H | OCH$_3$ | OCH$_3$ | H | >40 |
| 67 | H | H | H | OCH$_3$ | H | OCH$_3$ | 12 ± 3 |
| 68 | Cl | H | H | OCH$_3$ | H | H | 1.5 ± 0.01 |
| colchicine | | | | | | | 0.8 |

[a]ITP = inhibition of tubulin polymerization.

TABLE 5

The inhibitory effects of compounds 69 and 70 on platelet aggregation induced by thrombin, arachidonic acid (AA), collagen and platelet-activating factor (PAF)[a]

| Compounds ($\mu$g/ml) | Percent aggregation | | | |
|---|---|---|---|---|
| | thrombin | AA | collagen | PAF |
| Control | 92.9 ± 0.7(4) | 89.2 ± 0.9(5) | 90.3 ± 0.8(4) | 91.9 ± 0.6(4) |
| 69 100 | 2.8 ± 2.3(3)*** | 0.0 ± 0.0(4)*** | 0.0 ± 0.0(4)*** | 2.1 ± 1.8(4)*** |
| 50 | 13.3 ± 5.3(3)*** | | | 38.1 ± 8.3(4)*** |
| 20 | 88.1 ± 0.8(3)*** | | 0.0 ± 0.0(4)*** | 87.9 ± 1.8(4)*** |
| 10 | | 0.0 ± 0.0(4)*** | 1.1 ± 0.9(4)*** | |
| 5 | | 15.0 ± 11.8(4)*** | 31.5 ± 6.4(4)*** | |
| 2 | | 35.3 ± 14.9(4)*** | 43.0 ± 6.4(4)*** | |
| 1 | | 65.0 ± 8.1(4)*** | 52.6 ± 7.5(4)*** | |
| 0.5 | | 86.0 ± 1.2(4)*** | 76.2 ± 3.7(4)*** | |
| 0.2 | | | 88.4 ± 1.9(4)*** | |

TABLE 5-continued

The inhibitory effects of compounds 69 and 70 on platelet aggregation induced by thrombin, arachidonic acid (AA), collagen and platelet-activating factor (PAF)[a]

| Compounds | Percent aggregation | | | |
|---|---|---|---|---|
| (μg/ml) | thrombin | AA | collagen | PAF |
| $IC_{50}$ | | 7.20M | 8.47M | |
| Control | 92.9 ± 0.7(4) | 89.2 ± 0.9(5) | 90.3 ± 0.8(4) | 91.9 ± 0.6(4) |
| 70  100 | 11.7 ± 6.5(4)*** | 0.0 ± 0.0(5)*** | 0.0 ± 0.0(4)*** | 2.1 ± 1.8(4)*** |
| 50 | 75.1 ± 7.3(4)* | | 0.0 ± 0.0(4)*** | 19.8 ± 7.0(4)*** |
| 20 | 91.5 ± 1.2(4) | | 10.3 ± 6.0(4)*** | 88.8 ± 1.0(4)* |
| 10 | | | 19.3 ± 9.8(4)*** | |
| 5 | | | 30.1 ± 9.0(4)*** | |
| 2 | | | 35.0 ± 10.3(4)*** | |
| 1 | | 0.0 ± 0.0(5)*** | 47.1 ± 6.6(4)*** | |
| 0.5 | | 33.8 ± 13.4(5)*** | 63.9 ± 7.4(4)** | |
| 0.2 | | 76.9 ± 5.4(5)* | 78.5 ± 4.7(4)* | |
| 0.1 | | 85.5 ± 2.0(5) | 86.4 ± 2.9(4) | |
| $IC_{50}$ | | 1.60M | 9.20 μM | |

[a]Platelets were incubated with tested sample of 0.5% DMSO at 37° C. for 1 min, then thrombin (0.1 U/ml), AA (100 μM), collagen (10 μg/ml) or PAF (2 ng/ml) was added to trigger the aggregation.
Values are presented as mean ± S.E., n = 3–6.
*p < 0.05,
**P < 0.01,
***P < 0.001.

TABLE 6

The inhibitory effects of compounds 69 to 79 on platelet aggregation induced by arachidonic acid (in vitro)[a]

| Compounds | $R_{2''}$ | $R_{3''}$ | $R_{4''}$ | R | $IC_{50}$ (μM) |
|---|---|---|---|---|---|
| 69 | H | H | H | $CH_3$ | 7.20 |
| 70 | H | H | H | $C_2H_5$ | 1.60 |
| 71 | H | H | H | $CH_2COOEt$ | 26.95 |
| 72 | H | H | H | $(CH_2)_3COOEt$ | 30.65 |
| 73 | H | H | H | $(CH_2)_4COOEt$ | 173.43 |
| 74 | $OCH_3$ | H | H | $C_2H_5$ | 214.35 |
| 75 | H | $OCH_3$ | H | $C_2H_5$ | 69.29 |
| 76 | H | H | $OCH_3$ | $C_2H_5$ | 5.36 |
| 77 | H | H | H | $CH_3$ | 182.63 |
| 78 | H | H | H | $C_2H_5$ | 184.00 |
| 79 | H | H | H | CH2COOEt | >270 |
| Indomethacin | | | | | 0.25 |
| Aspirin | | | | | 20.00 |

[a]Platelets were incubated with a tested sample or 0.5% DMSO at 37° C. for 1 min, then AA (100 μM) was added to trigger aggregation.
Aspirin and Indomethacin are positive controls.
Values are expressed as means ± S.E. from 3 to 6 separations.

What is claimed is:

1. A 6,7,2',3',4',5'-substituted 2-phenyl-4-quinazolone having the formula(I)

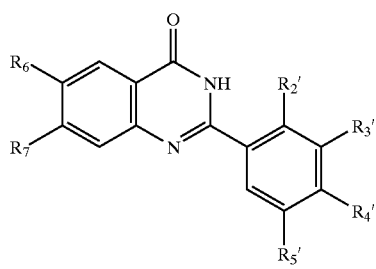

(I)

wherein
$R_{3'}$ is —$OCH_3$;
$R_{2'}$, $R_{4'}$ and $R_{5'}$ independently are H, $(CH_2)_nCH_3$, OH, $O(CH_2)_nCH_3$, X, or $NR_8R_9$, wherein n is an integer of 0–4, X is F, Cl, or Br, and $R_8$ and $R_9$ independently are H or $(CH_2)_nCH_3$, wherein n is defined as above;
$R_6$, is $(CH_2)_nCH_3$, OH, $O(CH_2)_nCH_3$, X, $NR_8R_9$,

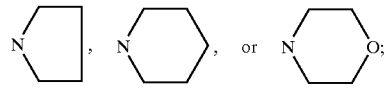

and
$R_7$ is H, $(CH_2)_nCH_3$, OH, $O(CH_2)_nCH_3$, X, $NR_8R_9$,

or $R_6$ and $R_7$ together is —$OCH_2O$—, wherein n, X, $R_8$ and $R_9$ are defined as above.

2. The 6, 7, 2',3',4',5'-substituted 2-phenyl-4-quinazolone according to claim 1, wherein $R_{2'}$, $R_{4'}$ and $R_{5'}$ independently are H or $O(CH_2)_nCH_3$, and at least one of $R_{2'}$, $R_{4'}$ and $R_{5'}$ is $O(CH_2)_nCH_3$, wherein n is an integer of 0–4.

3. The 6,7,2',3',4',5'-substituted 2-phenyl-4-quinazolone according to claims 1, wherein $R_6$ and $R_7$ independently are H, $O(CH_2)_nCH_3$, X, $NR_8R_9$,

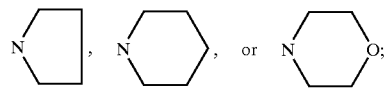

or $R_6$ and $R_7$ together is —$OCH_2O$—, wherein n, X, $R_8$ and $R_9$ are defined as in claim 1.

4. The 6,7,2',3',4',5'-substituted 2-phenyl-4-quinazolone according to claim 1, wherein $R_6$ and $R_7$ independently are H, $O(CH_2)_nCH_3$, X, $NR_8R_9$,

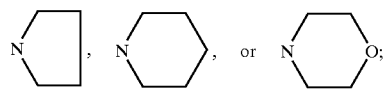

or $R_6$ and $R_7$ together is —OCH$_2$O—, wherein n, X, $R_8$ and $R_9$ are defined as in claim 1.

5. The 6,7,2',3',4',5'-substituted 2-phenyl-4-quinazolone according to claim 1, wherein $R_7$ is H, and $R_6$ is $NR_8R_9$,

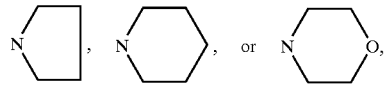

wherein $R_8$ and $R_9$ are defined as in claim 1.

6. The 6,7,2',3',4',5'-substituted 2-phenyl-4-quinazolone according to claim 5, wherein $R_8$ and $R_9$ are methyl.

7. The 6,7,2',3',4',5'-substituted, 2-phenyl-4-quinazolone according to claim 1, wherein $R_7$ is H, and $R_6$ is $NR_8R_9$,

wherein $R_8$ and $R_9$ are defined as in claim 1.

8. The 6,7,2',3',4',5'-substituted 2-phenyl-4-quinazolone according to claim 7, wherein $R_8$ and $R_9$ are methyl.

9. The 6,7,2',3',4',5'-substituted 2-phenyl-4-quinazolone according to claim 1, wherein $R_6$ and $R_7$ independently are H, methoxy or X, wherein X is defined as in claim 1.

10. A pharmaceutcal composition for the killing of soid tumor cells, which comprises a therapeutically effective amount of a 6,7,2',3',4',5'-substituted 2-phenyl-4-quinazolone of the formula (I) as set forth in any one of claim 1 to claim 9 or a pharmaceutically acceptable salt thereof, as an active ingredient, in admixture with a pharmaceutically acceptable carrier or diluent for the active ingredient, wherein the solid tumor cells comprise human ovarian cancer, ileocecal carcinoma, P-gp-expressing epidermoid carcinoma of the nasopharynix, or melanoma.

11. A method of killing solid tumor cells comprising administering a therapeutically effective amount of a 6,7,2',3',4',5'-substituted 2-phenyl-4-quinazolone of the formula (I) as set forth in any one of claim 1 to claim 9 to a subject having solid tumor cells, wherein the solid tumor cells comprise human ovarian cancer, ileocecal carcinoma, P-gp-expressing epidermoid carcinoma of the nasopharynx, or melanoma.

12. A 6,7,2',3',4',5'-substituted 2,3-dihydro-2-phenyl-4-quinazolone having the following formula (II):

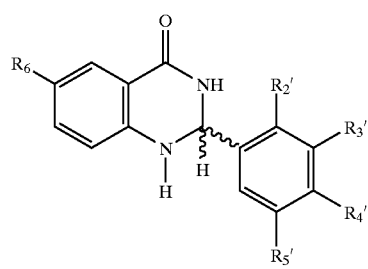

wherein
$R_3'$ is —OCH$_3$;
$R_2'$, $R_4'$ and $R_5'$ independently are H, (CH$_2$)$_n$CH$_3$, OH, O(CH$_2$)$_n$CH$_3$, X, or NR$_8$R$_9$, wherein X is F, Cl, or Br, and $R_8$ and $R_9$ independently are H or (CH$_2$)$_n$CH$_3$, wherein n is an integer of 0–4; and
$R_6$ and $R_7$ independently are H, (CH$_2$)$_n$CH$_3$, OH, O(CH$_2$)$_n$CH$_3$, X, NR$_8$R$_9$,

or $R_6$ and $R_7$ together is —OCH$_2$O—, wherein n, X, $R_8$ and $R_9$ are defined as above.

13. The 6,7,2',3',4',5'-substituted 2,3-dihydro-2-phenyl-4-quinazolone according to claim 12, wherein $R_7$ is H.

14. The 6,7,2',3',4',5'-substituted 2,3dihydro-2-phenyl-4-quinazolone according to claim 13, wherein $R_2'$, $R_4'$ and $R_5'$ independently are H or O(CH$_2$)$_n$CH$_3$, wherein n is defined as in claim 12.

15. The 6,7,2',3',4',5'-substituted 2,3-dihydro-2-phenyl-4-quinazolone according to claim 12, wherein $R_6$ is X, wherein X is defined as in claim 12.

16. The 6,7,2',3',4',5'-substituted 2,3-dihydro-2-phenyl-4-quinazolone according to claim 15, wherein X is Cl.

17. A pharmaceutical composition for the killing of solid tumor cells, which comprises a therapeutically effective amount of a 6,7,2',3',4',5'-substituted 2,3-dihydro-2-phenyl-4-quinazolone of theformula (II) as set forth in anyone of claim 12 to claim 16 or a pharmaceutically acceptable salt thereof, as an active ingredient, in admixture with a pharmaceutically acceptable carrier or diluent for the active ingredient, wherein the solid tumor cells comprise human ovarian cancer, ileocecal carcinoma, P-gp-expressing epidermoid carcinoma of the nasopharynx, or melanoma.

18. A method of killing solid tumor cells comprising administering a therapeutically effective amount of a 6,7,2',3',4',5'-substituted 2,3-dihydro-2-phenyl-4-quinazolone of the formula (II) as set forth in any one of claim 12 to claim 17 to a subject having solid tumor cells, wherein the solid tumor cells comprise human ovarian cancer, ileocecal carcinoma, P-gp-expressing epidermoid carcinoma of the nasopharynx, or melanoma.

19. A compound having a formula (III) as follows:

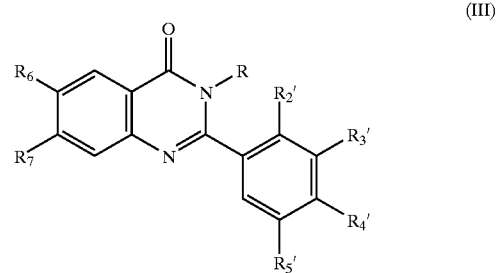

wherein
$R_2'$, $R_3'$, and $R_5'$ independently are H, (CH$_2$)$_n$CH$_3$, OH, O(CH$_2$)$_n$CH$_3$, X, or NR$_8$R$_9$, wherein n is an integer of 0–4, X is F, Cl, or Br, and $R_8$ and $R_9$ independently are H or (CH$_2$)$_n$CH$_3$, wherein n is defined as above;
$R_4'$, is (CH$_2$)$_n$CH$_3$, OH, O(CH$_2$)$_n$CH$_3$, X, or NR$_8$R$_9$, wherein n is an integer of 0–4, X is F, Cl, or Br, and $R_8$ and $R_9$ independently are H or (CH$_2$)$_n$CH$_3$, wherein n is defined as above;
R is (CH$_2$)$_n$CH$_3$, wherein n is defined as above; and $R_6$ and $R_7$ independently are H, $(CH_2)_nCH_3$, OH, $O(CH_2)_nCH_3$, X, $NR_8R_9$,

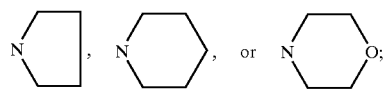

or $R_6$ and $R_7$ together is —$OCH_2O$—, wherein n, X, $R_8$ and $R_9$ are defined as above.

20. The compound according to claim 19, wherein $R_{5'}$, $R_6$ and $R_7$ are all H.

21. The compound of claim 20, wherein n is 0 or 1.

22. The compound of claim 21, having the formula (III).

23. The compound of claim 20, wherein R is $(CH_2)_nCH_3$, wherein n is 0 or 1.

24. The compound of claim 23, wherein $R_{2'}$, and $R_{4'}$ independently are H or $OCH_3$.

25. The compound of claim 24, wherein $R_{2'}$, and $R_{4'}$ are all H.

26. The compound of claim 24, wherein $R_{2'}$ is H, and $R_{4'}$ is $OCH_3$.

27. The compound of claim 26, wherein R is $CH_2CH_3$.

* * * * *